United States Patent [19]
Urakami et al.

[11] Patent Number: 5,491,329
[45] Date of Patent: Feb. 13, 1996

[54] PHOTODETECTING APPARATUS HAVING INTENSITY TUNEABLE LIGHT IRRADIATING UNIT

[75] Inventors: Tsuneyuki Urakami; Yutaka Tsuchiya, both of Hamamatsu, Japan

[73] Assignee: Hamamatsu Photonics K.K., Hamamatsu, Japan

[21] Appl. No.: 353,358

[22] Filed: Dec. 2, 1994

[30] Foreign Application Priority Data

Dec. 3, 1993 [JP] Japan ..................................... 5-304311

[51] Int. Cl.$^6$ ........................................................ G01J 1/32
[52] U.S. Cl. ............................................. 250/205; 250/574
[58] Field of Search ..................................... 250/205, 204, 250/574, 576, 214 C, 341.1, 339.07, 339.08, 358.1; 356/323, 336, 442; 128/664, 633, 665

[56] References Cited

U.S. PATENT DOCUMENTS

| | | | |
|---|---|---|---|
| 4,515,165 | 5/1985 | Carroll | 128/664 |
| 4,594,511 | 6/1986 | Cooper et al. | 250/341.1 |
| 4,972,331 | 11/1990 | Chance | 128/633 |

FOREIGN PATENT DOCUMENTS

| | | |
|---|---|---|
| 60-169725 | 9/1985 | Japan . |
| 4283679 | 10/1992 | Japan . |

OTHER PUBLICATIONS

Weng et al, "Measurement of Biological Tissue Metabolism Using Phase Modulation Spectroscopic Technology", SPIE Time–Resolved Spectroscopy and Imaging of Tissues, vol. 1431, Jan. 1991, pp. 161–169.

Primary Examiner—Edward P. Westin
Assistant Examiner—Que T. Le
Attorney, Agent, or Firm—Cushman Darby & Cushman

[57] ABSTRACT

Light the intensity of which is modulated to the initial intensity by a modulating signal having an ac component with a predetermined frequency and which is from the intensity tuneable light irradiating unit irradiates the scattering and absorption medium which is an object to be measured. The modulated light incident on the scattering and absorption medium propagates in the scattering and absorption medium, emerges therefrom and is incident to the photodetecting unit, and the photodetecting unit converts the incident light into an electric signal corresponding to the intensity of the incident light, and thereafter, outputs the electric signal as an optically detected signal. The feedback unit extracts the ac component from the input optically detected signal, and the intensity of the ac electric signal and the adjusting value are compared and the variation of the quantity of generating light is sent to the intensity tuneable light irradiating unit. Then, the phase difference detection is performed as the gain of the photodetecting means is fixed and the intensity of the ac component having a modulation frequency emitted from the photodetecting means is maintained so as to substantially match with the preset adjusting value.

18 Claims, 12 Drawing Sheets

PHOTODETECTING APPARATUS HAVING INTENSITY TUNEABLE LIGHT IRRADIATING UNIT

BACKGROUND OF THE INVENTION

1. Field of the Invention

The present invention relates to a photodetecting apparatus to be utilized in measurement of internal information relative to light in a scattering and absorption medium.

2. Related Background Art

Techniques of non-invasive measurement of an absorption coefficient or a transport scattering coefficient in a scattering and absorption medium by irradiating the scattering and absorption medium such as a living body with light such as pulsed light or continuous light and detecting light diffused during propagation in the scattering and absorption medium and thereafter emerging therefrom have been drawing attention. Especially, a method for obtaining internal information in the scattering and absorption medium by using pulsed light or intensity-modulated light as irradiation light, measuring a timing difference or a phase difference between the irradiation light and light emerging from the scattering and absorption medium after the irradiation light is diffused during propagation therein, and obtaining the internal information in the scattering and absorption medium from the information of phase difference is most effective among such techniques.

An apparatus utilizing this method is, for example, disclosed in "B. Chance: PHASE MODULATION SPECTROPHOTOMETRY, U.S. Pat. No. 4,972,331". This apparatus is irradiating a scattering and absorption medium such as a living body with modulated light resulting from modulating the intensity of light having a plurality of predetermined wavelengths by a predetermined modulation frequency, detecting light emerging therefrom with a photomultiplier tube (PMT) thereby to measure a phase difference between a phase of an ac component having a modulation frequency of modulated light upon irradiation and a phase of an ac component having a modulation frequency of detected light upon detection.

In the above-described photodetection, it is considered that an S/N ratio of the optically detected signal is proportional to the one half power of the number of detected photons. Accordingly, in the above-described apparatus, light having a wavelength at which the number of photons to be detected becomes the smallest, that is, light having a wavelength at which the intensity of output light becomes the smallest upon irradiation with the same light intensity, or modulated light with intensity at which the sufficient S/N ratio can be obtained for any kinds of scattering media needs to irradiate an object to be measured. With this radiation, a method for adjusting a gain of the photodetecting apparatus so that the optically detected signal is amplified to be readily processed later can be considered; however, in the photodetecting unit, a time between a light input and an output of an optically detected signal is different depending upon the gain. For example, the gain of the photomultiplier tube is adjusted by varying an applied voltage, but the variation of the applied voltage means the variation of the acceleration voltage, which changes the time between the light input and the output of the optically detected signal. Further, the gain of an avalanche photodiode (APD) is adjusted by varying a bias voltage, but the time between the light input and the output of the optically detected signal is varied because of variation of the bias voltage. FIG. 1 is a graph showing a relation between a bias voltage and a phase at a modulation frequency when one avalanche photodiode on the market is used and modulated light the intensity of which is modulated by a frequency of 40 MHz irradiates the avalanche photodiode. As shown in the graph, the phase difference is higher than 60° at maximum depending on the bias voltage.

Therefore, for the stable measurement of the timing difference or phase difference, prior to the measurement, a function of gain of the photodetecting unit and time between the light input and the output of the optically detected signal needs to be precisely measured, and the timing difference or phase difference needs to be compensated for every gain upon the measurement.

SUMMARY OF THE INVENTION

It is an object of the present invention to provide a photodetecting apparatus which can readily and accurately measure a phase difference between an optical signal the intensity of which is modulated and which irradiates an scattering and absorption medium and an optical signal emerging through the scattering and absorption medium.

A photodetecting apparatus of the present invention assures an S/N ratio of an optically detected signal by maintaining the number of photons incident on a photodetecting unit, and carries out the photodetecting operation as a gain of the photodetecting unit is fixed.

A first photodetecting apparatus of the present invention comprises (a) intensity tuneable light irradiating means for generating light to irradiate a scattering and absorption medium, an intensity of the light being modulated by a modulating signal having an ac component with a predetermined frequency, an amount of modulation of generating light or a quantity of generating light being adjustable in accordance with an external instruction, (b) photodetecting means for detecting an optical signal having a component with the predetermined frequency emerging from the scattering and absorption medium after the optical signal is generated from the intensity tuneable light irradiating means, irradiates the scattering and absorption medium and propagates in the scattering and absorption medium, (c) feedback means for receiving an optically detected signal corresponding to the intensity of the optical signal emitted from the photodetecting means, sending an instruction to the intensity tuneable light irradiating means to increase the quantity of generating light or to increase the amount of modulation of generating light when the intensity of an ac component of the optically detected signal detected by the photodetecting means is smaller than a predetermined value, and sending an instruction to the intensity tuneable light irradiating means to decrease the quantity of generating light or to decrease the amount of modulation of generating light when the intensity of the ac component of the optically detected signal detected by the photodetecting means is larger than the predetermined value, and (d) processing means for receiving the modulating signal and the optically detected signal and obtaining one of a timing difference between the modulating signal and the optically detected signal, and a phase difference between the modulating signal and the optically detected signal.

A second photodetecting apparatus of the present invention comprises (a) intensity tuneable light irradiating means for generating a first number of lights each having a different predetermined wavelength to irradiate a scattering and absorption medium, an intensity of each the light being modulated by a modulating signal having an ac component with a predetermined frequency, an amount of modulation of generating light or a quantity of generating light being adjustable in accordance with an external instruction, (b) light branching means for receiving optical signals each having the predetermined frequency component emerging from the scattering and absorption medium after the optical signals are generated from the intensity tuneable light irradiating means, irradiate the scattering and absorption medium and propagate in the scattering and absorption medium, and branching the optical signals into the first number of lights each having the predetermined wavelength, (c) photodetecting means comprising the first number of photodetecting units arranged for each the light having the predetermined wavelength, for detecting light emitted from the light branching means, (d) feedback means for receiving an optically detected signal for each the predetermined wavelength corresponding to the intensity of the optical signal for each the predetermined wavelength emitted from the photodetecting means, sending an instruction to the intensity tuneable light irradiating means to increase the quantity of generating light having the respective wavelength or to increase the amount of modulation of generating light having the respective wavelength when the intensity of an ac component of the optically detected signal detected by the photodetecting means is smaller than a predetermined value, and sending an instruction to the intensity tuneable light irradiating means to decrease the quantity of generating light having the respective wavelength or to decrease the amount of modulation of generating light having the respective wavelength when the intensity of the ac component of the optically detected signal detected by the photodetecting means is larger than the predetermined value, and (e) processing means for receiving the modulating signal and the optically detected signals and obtaining one of a timing difference between the modulating signal and the optically detected signal, and a phase difference between the modulating signal and the optically detected signal, for each the predetermined wavelength.

The tuneable light irradiating means may generate pulse light.

The intensity tuneable light irradiating means can comprise (1) a modulating signal generating unit for generating the modulating signal on which the ac component with the predetermined frequency is superimposed, (2) light source means for receiving the modulating signal, and generating light the intensity of which is modulated by the predetermined frequency, and (3) a light transmittivity varying unit for varying light transmittivity in accordance with a quantity-of-irradiation-light indicating signal sent from the feedback means. Alternatively, the intensity tuneable light irradiating means can comprise (1) a modulating signal generating unit for generating the modulating signal on which the ac component with the predetermined frequency is superimposed and which has an amplitude corresponding to a quantity-of-irradiation-light indicating signal sent from the feedback means, and (2) light source means for receiving the modulating signal and generating light the intensity of which is modulated by the predetermined frequency.

The light source means can comprise a light emitting unit for generating light having a variable wavelength. Alternatively, the light source means can comprise (1) a plurality of light emitting units, each generating light having a different wavelength, and (2) a light selecting unit for selecting and taking out one of lights generated from the plurality of the light emitting units.

The processing means can comprise (1) a reference signal generating unit for generating a reference signal having a reference frequency different from the predetermined frequency, (2) a first signal converter for receiving the reference signal and the modulating signal, calculating a product of both signals, and thereafter generating a signal having a frequency difference between the reference frequency and the predetermined frequency and including phase information of the modulating signal against the reference signal, and (3) a second signal converter for receiving the reference signal and the optically detected signal, calculating a product of both signals, and thereafter generating a signal having a frequency difference between the reference frequency and the predetermined frequency and including phase information of the modulating signal against the reference signal, and the processing means obtains one of the timing difference between the modulating signal and the optically detected signal, and the phase difference between the modulating signal and the optically detected signal, based on a waveform of the output signal of the first signal converter and a waveform of the output signal of the second signal converter.

In the first photodetecting apparatus of the present invention, prior to measurement, the gain of the photodetecting means is determined. Then, with this gain, the time between the light incident and the output of the optically detected signal in the photodetecting means is measured and stored in the processing means. At the same time, an adjusting value for the intensity of the ac component of the optically detected signal is determined and set in the feedback means. After these preparation, the photodetecting operation to obtain the timing difference or the phase difference is started.

First, light the intensity of which is modulated to the initial intensity by a modulating signal having an ac component with a predetermined frequency and which is from the intensity tuneable light irradiating means irradiates the scattering and absorption medium which is an object to be measured. The ac component of the modulating signal is also applied to the processing means. The modulated light incident on the scattering and absorption medium propagates in the scattering and absorption medium, emerges therefrom and is incident to the photodetecting means. The photodetecting means converts the incident light into an electric signal (a voltage signal or a current signal) corresponding to the intensity of the incident light, and thereafter, outputs the electric signal as an optically detected signal. The optically detected signal output from the photodetecting means is sent to the feedback means and the processing means.

The feedback means extracts the ac component from the input optically detected signal. If the intensity of the ac electric signal is smaller than the adjusting value, the feedback means sends an instruction to the intensity tuneable light irradiating means to increase the quantity of generating light, and if the intensity of the ac electric signal is larger than the adjusting value, it sends an instruction to the intensity tuneable light irradiating means to decrease the quantity of generating light. The intensity of output light from the intensity tuneable light irradiating means is controlled with operations in the feedback loop of the intensity tuneable light irradiating means—the photodetecting means—the feedback means—the intensity tuneable light irradiating means. Then, as the gain of the photodetecting means is fixed, the intensity of the ac component having a modulation frequency emitted from the photodetecting means is maintained so as to substantially match with the preset adjusting value.

After the intensity of the ac component of the optically detected signal emitted from the photodetecting means substantially matches with the adjusting value, the processing means processes the ac component of the modulating signal and the ac component of the optically detected signal to obtain the timing different between the modulating signal and the optically detected signal, or the phase difference between the modulating signal and the optically detected signal. In the processing means, if the product of the oscillating signal with the reference frequency and the modulating signal, and the product of the oscillating signal and the optically detected signal are calculated, and the signal having a frequency difference between the frequency of the modulating signal and the frequency of the optically detected signal, and the signal having a frequency difference between the frequency of the optically detected signal and the reference frequency are processed, the handling frequency would be lowered, so that the measurement with high precision is readily possible.

In the second photodetecting apparatus of the present invention, in the same as the first photodetecting apparatus of the present invention, prior to measurement, the gain of the photodetecting units arranged for each predetermined wavelength in the photodetecting means is determined, and with this gain, time between the light incident and the output of the optically detected signal in the photodetecting means is measured for each predetermined wavelength and stored in the processing means. At the same time, an adjusting value for the intensity of the ac component of the optically detected signal is determined and stored in the feedback means. After these preparation, the photodetecting operation to obtain the timing difference or the phase difference is started.

First, lights the intensity of which are modulated to the initial intensity by a respective modulating signal having an ac component with a respective predetermined frequency, and which is from the intensity tuneable light irradiating means irradiate the scattering and absorption medium which is an object to be measured. The ac component of the modulating signal for each wavelength is also applied to the processing means. The modulated lights are incident on the scattering and absorption medium, propagate in the scattering and absorption medium, emerge therefrom and are incident to the light branching means. The light branching means branches incident lights into lights each having a respective predetermined wavelength and outputs the lights. The photodetecting means converts the lights into electric signals (voltage signals or current signals) corresponding to the intensity of the incident light for each wavelength, and thereafter, outputs the electric signal as an optically detected signal for each wavelength. The optically detected signal emitted from the photodetecting means is sent to the feedback means and the processing means for each predetermined signal.

The feedback means extracts the ac component from the input optically detected signal for each predetermined wavelength. For each predetermined wavelength, if the intensity of the ac electric signal is smaller than the respective adjusting value, the feedback means sends an instruction to the intensity tuneable light irradiating means to increase the quantity of generating light having the respective predetermined wavelength, and if the intensity of the ac electric signal is larger than the respective adjusting value, it sends an instruction to the intensity tuneable light irradiating means to decrease the quantity of generating light having the respective predetermined wavelength. For each predetermined wavelength, the intensity of output light from the intensity tuneable light irradiating means is controlled with operations in the feedback loop of the intensity tuneable light irradiating means—the photodetecting means—the feedback means—the intensity tuneable light irradiating means. Then, as the gain of the photodetecting means is fixed for each predetermined wavelength, for each predetermined wavelength, the intensity of the ac component having a modulation frequency emitted from the photodetecting means is maintained so as to substantially match with the preset adjusting value.

After the intensity of the ac component of the optically detected signal emitted from the photodetecting means substantially matches with the adjusting value, for each predetermined wavelength, the processing means processes the ac component of the modulating signal and the ac component of the optically detected signal for each predetermined wavelength to obtain the timing difference between the modulating signal and the optically detected signal, or the phase difference between the modulating signal and the optically detected signal for all predetermined wavelengths at the same time. In the processing means, if the product of the oscillating signal with the reference frequency and the modulating signal, and the product of the oscillating signal and the optically detected signal are calculated for each wavelength, and the signal having a frequency difference between the frequency of the modulating signal and the reference frequency, and the signal having a frequency difference between the frequency of the optically detected signal and the reference frequency is processed, the handling frequency would be lowered, so that the measurement with high precision is readily possible.

The present invention will become more fully understood from the detailed description given hereinbelow and the accompanying drawings which are given by way of illustration only, and thus are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

Figure 1:
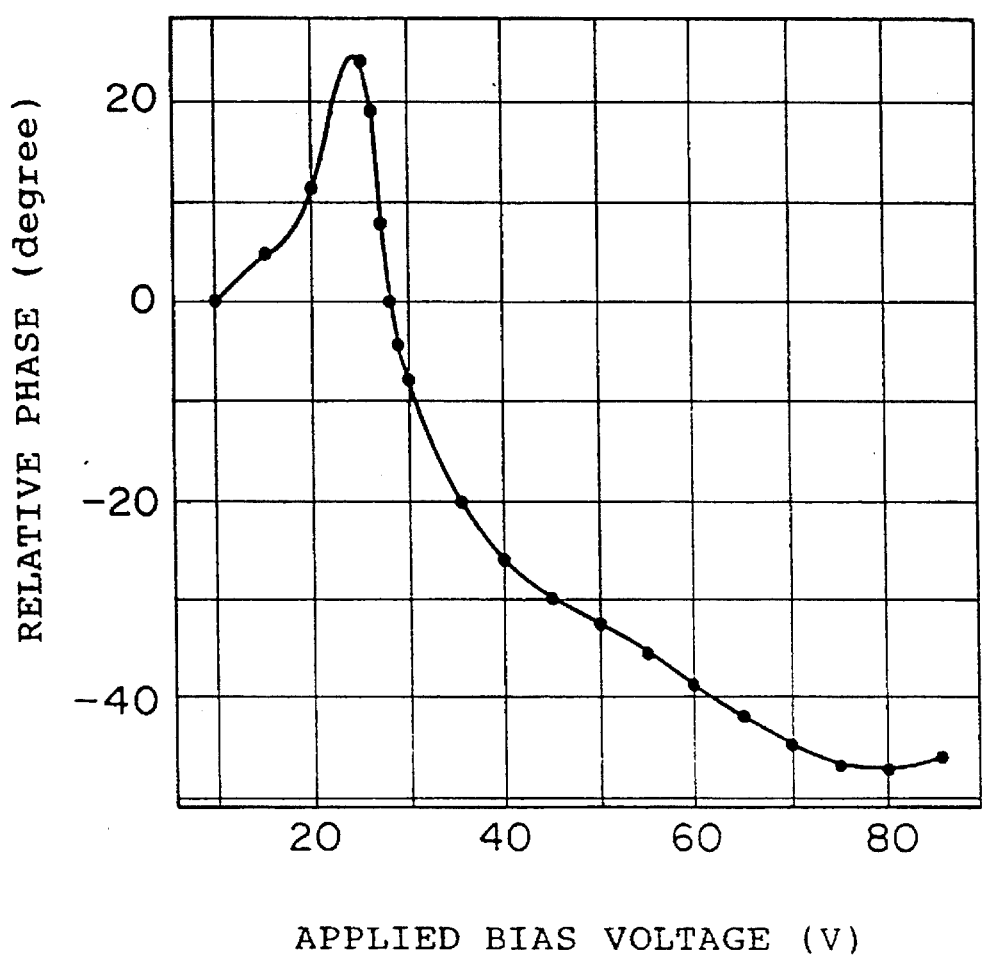
FIG. 1 is a graph of results of measurement of a delay property of an avalanche photodiode.

The embodiments of the present invention will be described with reference to the accompanying drawings. In the description of drawings, the same components are represented by the same reference numerals, and the repetitive description on the same components is omitted.

(First Embodiment)

Figure 2:
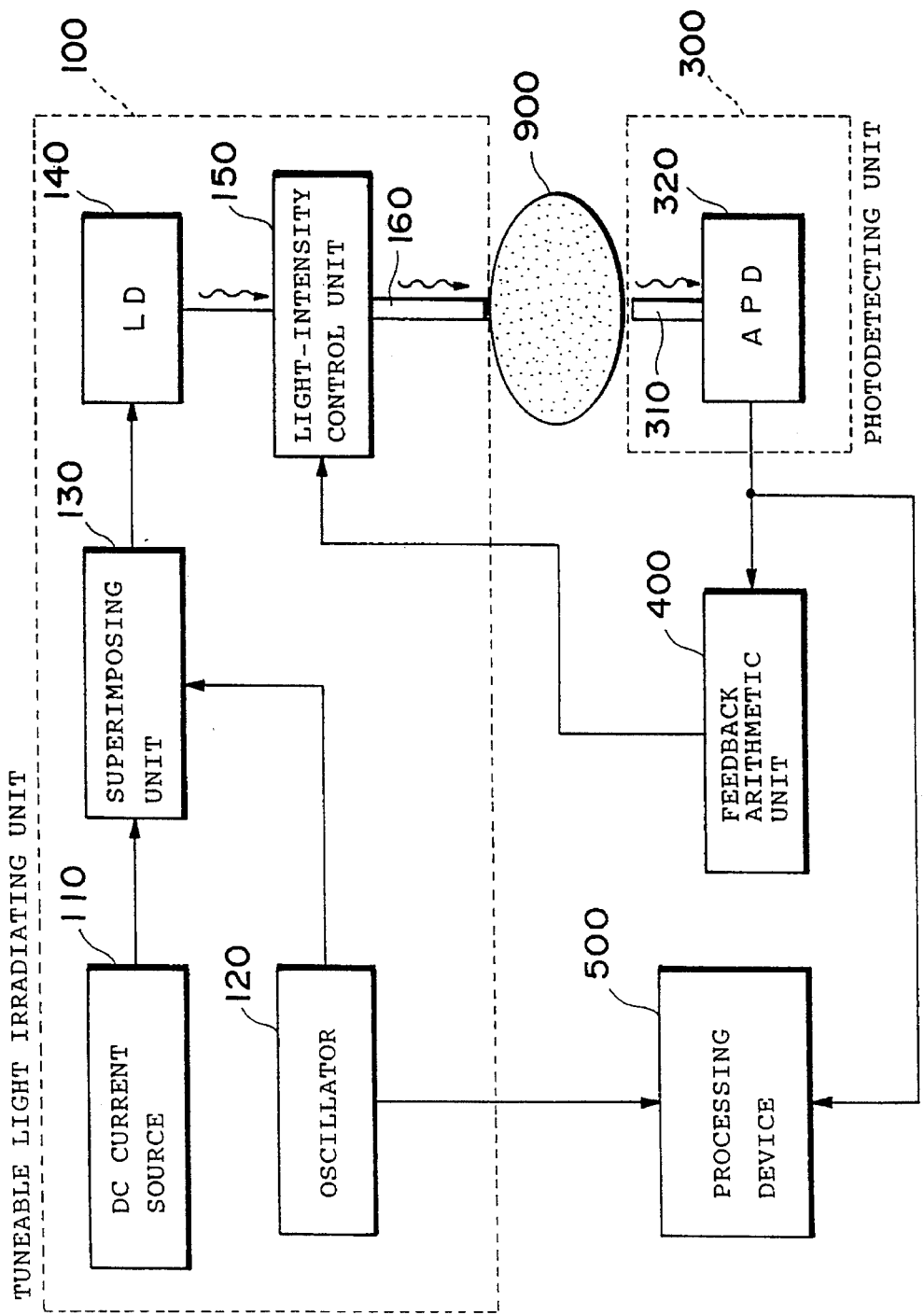
FIG. 2 is a block diagram of a photodetecting apparatus of the first embodiment of the present invention.

FIG. 2 is a block diagram of a photodetecting apparatus of the first embodiment according to the present invention. As shown in FIG. 2, the photodetecting apparatus of the present embodiment comprises (a) a intensity tuneable light irradiating unit 100 for generating light, the intensity of which is modulated by a modulating signal having an ac component with a predetermined frequency, to irradiate a scattering and absorption medium 900, the quantity of generating light being adjustable by an external instruction, (b) a photodetecting unit 300 comprising an avalanche photodiode for detecting an optical signal having a predetermined frequency emerging from the scattering and absorption medium 900 after the optical signal is generated from intensity tuneable light irradiating unit 100, irradiates the scattering and absorption medium 900, and propagates therein, (c) a feedback unit comprising a feedback arithmetic unit 400 for receiving an optically detected signal corresponding to an intensity of an optical signal emitted from the photodetecting unit 300, sending an instruction to the intensity tuneable light irradiating unit 100 to increase a quantity of generating light when the intensity of the ac component of the optical signal detected by the photodetecting unit 300 is smaller than a predetermined value, and sending an instruction to the intensity tuneable light irradiating unit 100 to decrease the quantity of generating light when the intensity of the optical signal detected by the photodetecting unit 300 is larger than the predetermined value, and (d) a processing device 500 for receiving the modulating signal and the optically detected signal, and obtaining a phase difference between the modulating signal and the optically detected signal.

Figure 3:
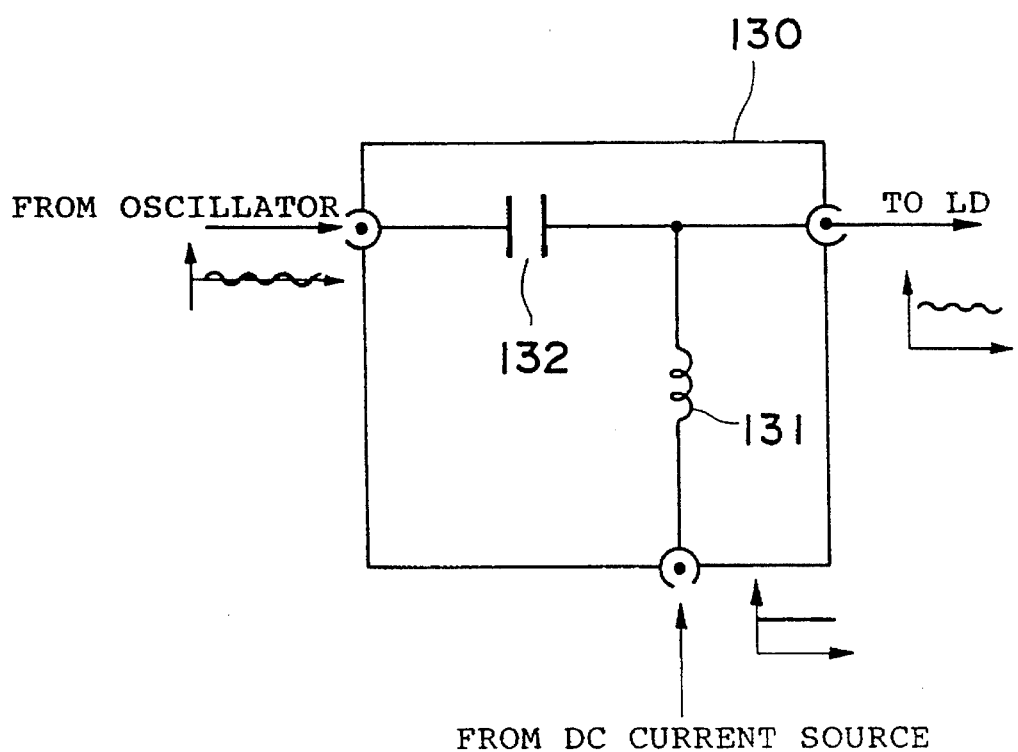
FIG. 3 is a circuit diagram of a current adder.
Figure 4:
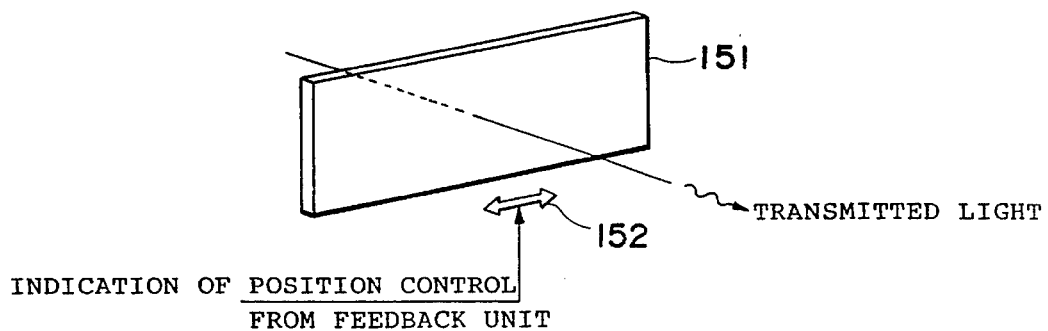
FIG. 4–FIG. 6 are views of configuration of a light-intensity control unit.
Figure 5:
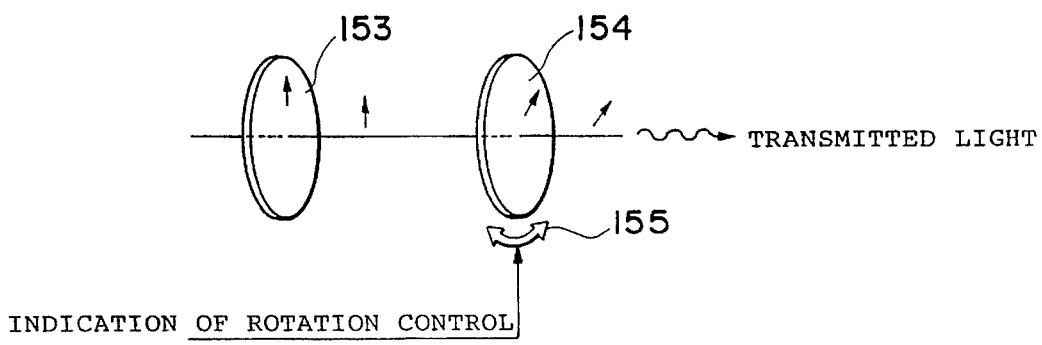
Figure 6:
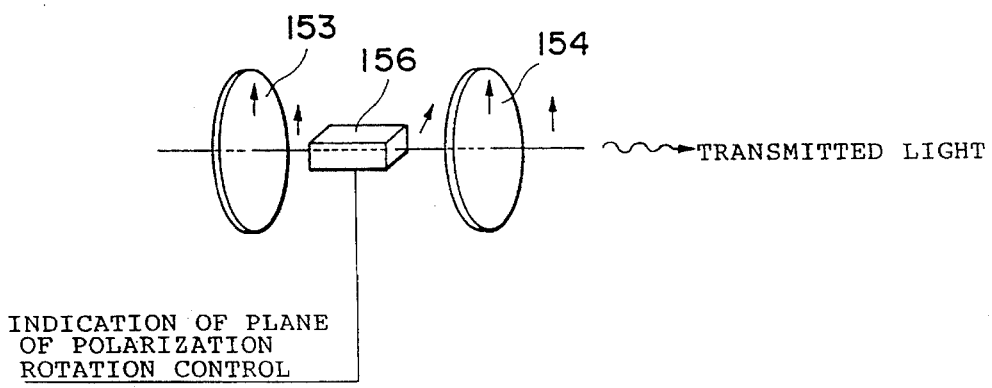

Here, the intensity tuneable light irradiating unit 100 comprises (1) a dc current source 110 for supplying dc current, (2) an oscillator 120 for generating an ac signal having a modulation frequency, (3) a superimposing unit 130 for superimposing the ac signal generated from the oscillator 120 on the dc current generated from the dc current source 110, (4) a laser diode 140 for receiving a modulating signal generated from the superimposing unit 130 and emitting intensity-modulated light, (5) a light-intensity control unit 150 for receiving the intensity-modulated light and transmitting light with a transmittivity indicated from outside, and (6) an optical fiber cable 160 for guiding irradiation light emitted from the light-intensity control unit 150 to the surface of the scattering and absorption medium 900. FIG. 3 is a circuit diagram of the superimposing unit 130. The superimposing unit 130 comprises a coil 131 and a condenser 132, the one terminals of which are connected together, and the dc signal is applied to the other terminal of the coil 131 and the ac signal is applied to the other terminal of the condenser 132. Then, an superimposed current signal is generated from the node. There is a circuit having an equivalent circuit configuration of this circuit, namely, bias T. FIGS. 4–6 show a configuration of the light-intensity control unit which is usable in the present embodiment. FIG. 4 shows a configuration of the light-intensity control unit 150 of the present embodiment. The light-intensity control unit 150 comprises an ND filter 151 in which the transmittivity is continuously changed point by point, and a filter moving unit 152 for moving the location of the ND filter 151 in accordance with the external instruction. FIG. 5 shows a configuration of the first modification of the light-intensity control unit. This light-intensity control unit comprises two polarizers 153 and 154, and a plane-of-polarization rotating unit 155 for the polarizer 154 for controlling an angle of transmission-polarization direction in accordance with the external instruction. FIG. 6 shows a configuration of the second modification of the light-intensity control unit. This light-intensity control unit comprises two polarizers 153 and 154, and a plane-of-polarization rotating unit 156 which is provided between the two polarizers and which comprises an EO modulator for varying an amount of rotation of plane of polarization in accordance with the external instruction. Note that if a plurality of filters each having a different refractive index or a different thickness is used for controlling light intensity, a phase may be varied. Therefore, a light-intensity control unit which does not cause a variation of an output phase, which affects the measurement precision, needs to be selected.

The photodetecting unit 300 comprises an optical fiber cable 310 for receiving an optical signal emerging from the scattering and absorption medium 900, and an avalanche photodiode 320 for receiving an optical signal emerging from the optical fiber cable 310 and converting the optical signal into an electric signal.

Figure 7:
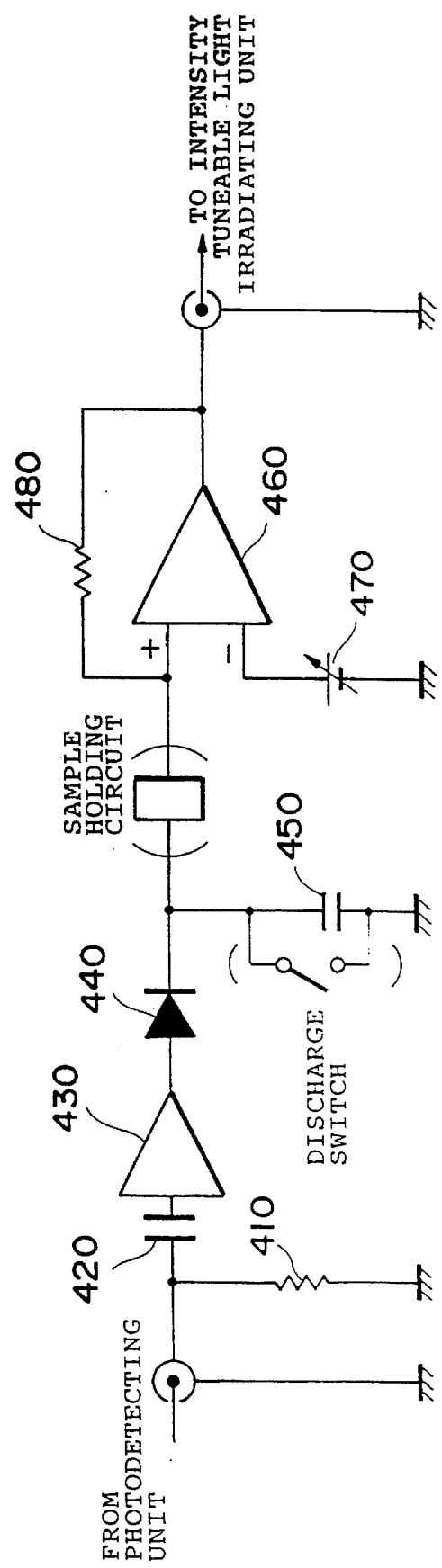
FIG. 7 is a circuit diagram of a feedback unit.

FIG. 7 is a circuit diagram of the feedback arithmetic unit 400. An optically detected signal (a current signal flowing through the avalanche photodiode) applied to the feedback arithmetic unit 400 is converted into a voltage signal by a resistor 410. An ac component of the voltage signal is applied to a high frequency amplifier 430 through a condenser 420. An amplified signal output from the high frequency amplifier 430 is half-wave-rectified by a diode 440. A rectified current is charged in a condenser 450 as charges, and the voltage corresponding to the accumulated charges is transmitted to a + input terminal of an operational amplifier 460. On the other hand, a voltage supplied from a variable dc voltage source 470 is supplied to a − input terminal of the operational process amplifier 460. The output terminal and the + input terminal, of the operational amplifier are connected through a resistor 480. Then, with the voltage supplied from the variable dc voltage source 470 as a reference voltage, voltage proportional to a difference between the reference voltage and the voltage transmitted to the + input terminal is generated from the operational amplifier 460. Note that a discharge switch or a sample holding circuit inside parentheses in FIG. 7 can be added to the circuit, by which the measurement precision is further improved.

The measurement of the phase difference with the photodetecting apparatus of the present embodiment is carried out as follows.

Prior to the measurement, the gain of the photodetecting unit 300 is determined and the bias voltage to be this gain is applied to the avalanche photodiode 320. Then, with this gain, the time between the light input and the output of the optically detected signal in the photodetecting unit 300 is measured and stored in the processing device 500. At the same time, an adjusting value for the intensity of the ac component of the optically detected signal is determined, and the reference voltage is set by adjusting the variable dc voltage source 470 in the feedback arithmetic unit 400. After these preparation, the photodetecting operation to obtain the phase difference is started.

First, light the intensity of which is modulated to the initial intensity by a modulating signal having an ac component with a predetermined frequency and which is from the intensity tuneable light irradiating means 100 irradiates the scattering and absorption medium 900 which is an object to be measured. The ac component of the modulating signal is also applied to the processing device 500. The modulated light incident on the scattering and absorption medium 900 propagates in the scattering and absorption medium 900, emerges therefrom and is incident to the photodetecting unit 300. The photodetecting unit 300 converts the incident light into an electric signal (current signal) corresponding to the intensity of the incident light, and thereafter, outputs the electric signal as an optically detected signal. The optically detected signal output from the photodetecting unit 300 is transmitted to the feedback arithmetic unit 400 and the processing device 500.

The feedback arithmetic unit 400 extracts the ac component from the input optically detected signal. If the intensity of the ac electric signal is smaller than the adjusting value, the feedback arithmetic unit 400 sends an instruction to the light-intensity control unit 150 in the intensity tuneable light irradiating unit 100 to increase a quantity of transmitting light, and if the intensity of the ac electric signal is larger than the adjusting value, it sends an instruction to the quantity-of-light control unit 150 to decrease the quantity of transmitting light. The intensity of output light from the intensity tuneable light irradiating unit 100 is controlled with operations in the feedback loop of the intensity tuneable light irradiating unit 100—the photodetecting unit 300—the feedback arithmetic unit 400—the intensity tuneable light irradiating unit 100. Then, as the gain of the avalanche photodiode 320 in the photodetecting unit 300 is fixed, the intensity of the ac component having a modulation frequency emitted from the photodetecting unit 300 is maintained so as to substantially match with the preset adjusting value.

After the intensity of the ac component of the optically detected signal emitted from the photodetecting unit 300 substantially matches with the adjusting value, the processing device 500 processes the ac component of the modulating signal and the ac component of the optically detected signal to obtain the phase difference between the modulating signal and the optically detected signal. The timing difference between the modulating signal and the optically detected signal can also be calculated from the results of the phase difference measurement.

(Second Embodiment)

Figure 8:
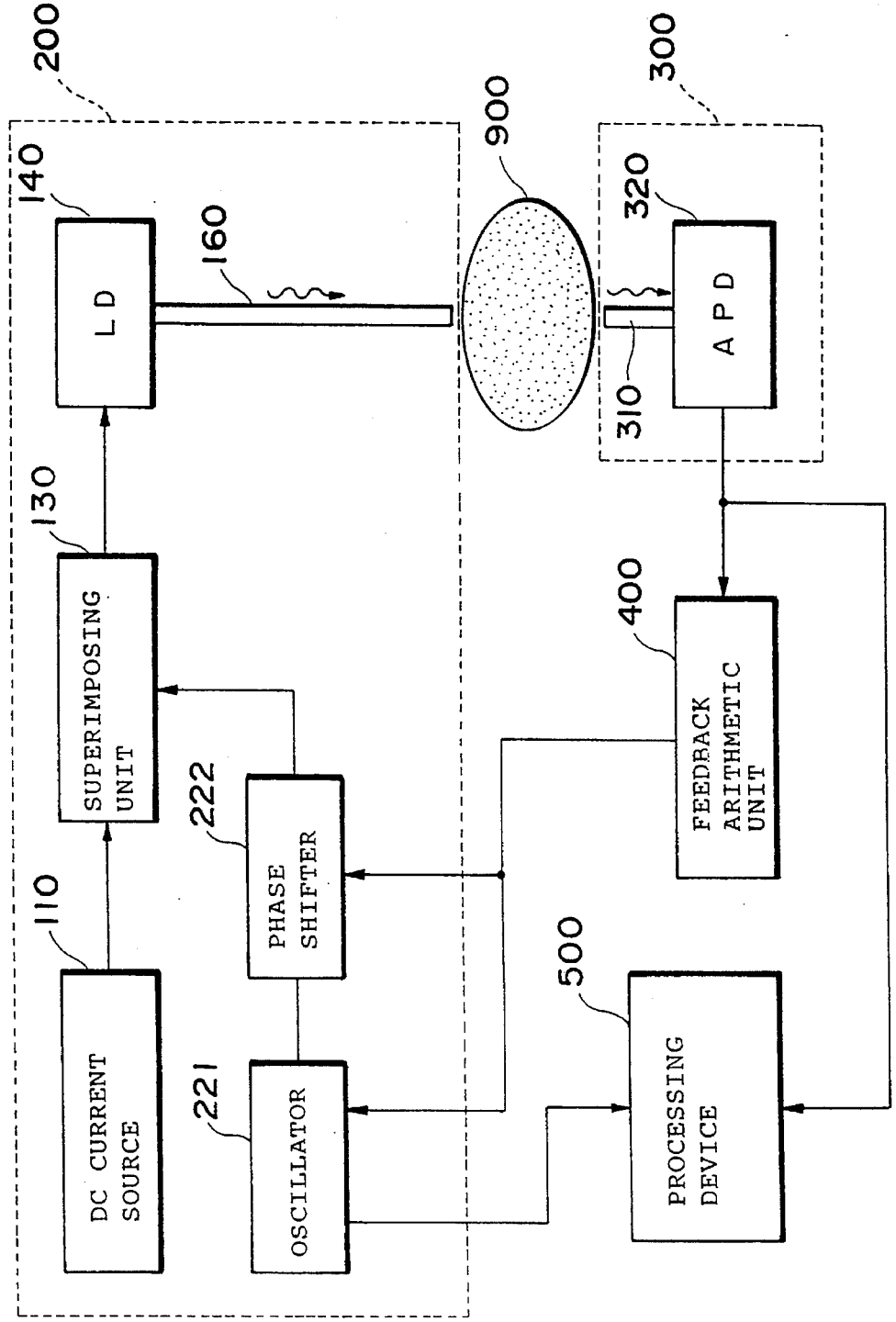
FIG. 8 is a block diagram of a photodetecting apparatus of the second embodiment of the present invention.

FIG. 8 is a block diagram of a photodetecting apparatus of the second embodiment of the present invention. The photodetecting apparatus of the present embodiment has the same configuration as the apparatus of the first embodiment except that a intensity tuneable light irradiating unit 200 is different from the intensity tuneable light irradiating unit 100 of the first embodiment.

The intensity tuneable light irradiating unit 200 of the photodetecting apparatus of the present embodiment comprises (1) a dc current source 110 for supplying dc current, (2) an oscillator 221 for generating an ac signal having a modulation frequency and an amplitude controlled in accordance with an external instruction, (3) a phase shifter 222 for receiving an ac signal from the oscillator 221 and compensating a variation of phase due to the amplitude of the signal generated from the oscillator 221 by controlling an amount of variation of the phase in accordance with the external instruction, (4) a superimposing unit 130 for superimposing the ac signal output from the phase shifter 222 on the dc current output from the dc current source 110, (5) a laser diode 140 for receiving a modulating signal output from the superimposing unit 130 and emitting intensity-modulated light, and (6) an optical fiber cable 160 for guiding irradiation light emitted from diode 140 to the surface of the scattering and absorption medium 900.

The measurement of the phase difference with the photodetecting apparatus of the present embodiment is carried out as follows.

In the same way as the first embodiment, prior to the measurement, the gain of the photodetecting unit 300 is determined and the bias voltage to be this gain is applied to the avalanche photodiode 320. Then, with this gain, the time between the light input and the output of the optically detected signal in the photodetecting unit 300 is measured and stored in the processing device 500. At the same time, an adjusting value for the intensity of the ac component of the optically detected signal is determined, and the reference voltage is set by adjusting the variable dc voltage source 470 in the feedback arithmetic unit 400. After these preparation, the photodetecting operation to obtain the phase difference is started.

First, light the intensity of which is modulated to the initial intensity by a modulating signal having an ac component with a predetermined frequency and which is from the intensity tuneable light irradiating means 200 irradiates the scattering and absorption medium 900 which is an object to be measured. The ac component of the modulating signal is also applied to the processing device 500. The modulated light incident on the scattering and absorption medium 900 propagates in the scattering and absorption medium 900, emerges therefrom and is incident to the photodetecting unit 300. The photodetecting unit 300 converts the incident light into an electric signal (current signal) corresponding to the intensity of the incident light, and outputs the electric signal as an optically detected signal. The optically detected signal output from the photodetecting unit 300 is transmitted to the feedback arithmetic unit 400 and the processing device 500.

The feedback arithmetic unit 400 extracts the ac component from the input optically detected signal. If the intensity of the ac electric signal is smaller than the adjusting value, the feedback arithmetic unit 400 sends an instruction to the oscillator 221 in the intensity tuneable light irradiating unit 200 to increase an amplitude of a generating signal and sends an instruction to the phase shifter 222 to compensate a phase, and if the intensity of the ac electric signal is larger than the adjusting value, it sends an instruction to the oscillator 221 in the intensity tuneable light irradiating unit 200 to decrease the amplitude of a generating signal and sends an instruction to the phase shifter 222 to compensate the phase. The intensity of output light from the intensity tuneable light irradiating unit 200 is controlled with operations in the feedback loop of the intensity tuneable light irradiating unit 200—the photodetecting unit 300—the feedback arithmetic unit 400—the intensity tuneable light irradiating unit 200. Then, as the gain of the avalanche photodiode 320 in the photodetecting unit 300 is fixed, the intensity of the ac component having a modulation frequency emitted from the photodetecting unit 300 is maintained so as to substantially match with the preset adjusting value.

In the same way as the first embodiment, after the intensity of the ac component of the optically detected signal emitted from the photodetecting unit 300 substantially matches with the adjusting value, the processing device 500 processes the ac component of the modulating signal and the ac component of the optically detected signal to obtain the phase difference between the modulating signal and the optically detected signal. The timing difference between the modulating signal and the optically detected signal can also be calculated from the results of the phase difference measurement.

(Third Embodiment)

Figure 9:
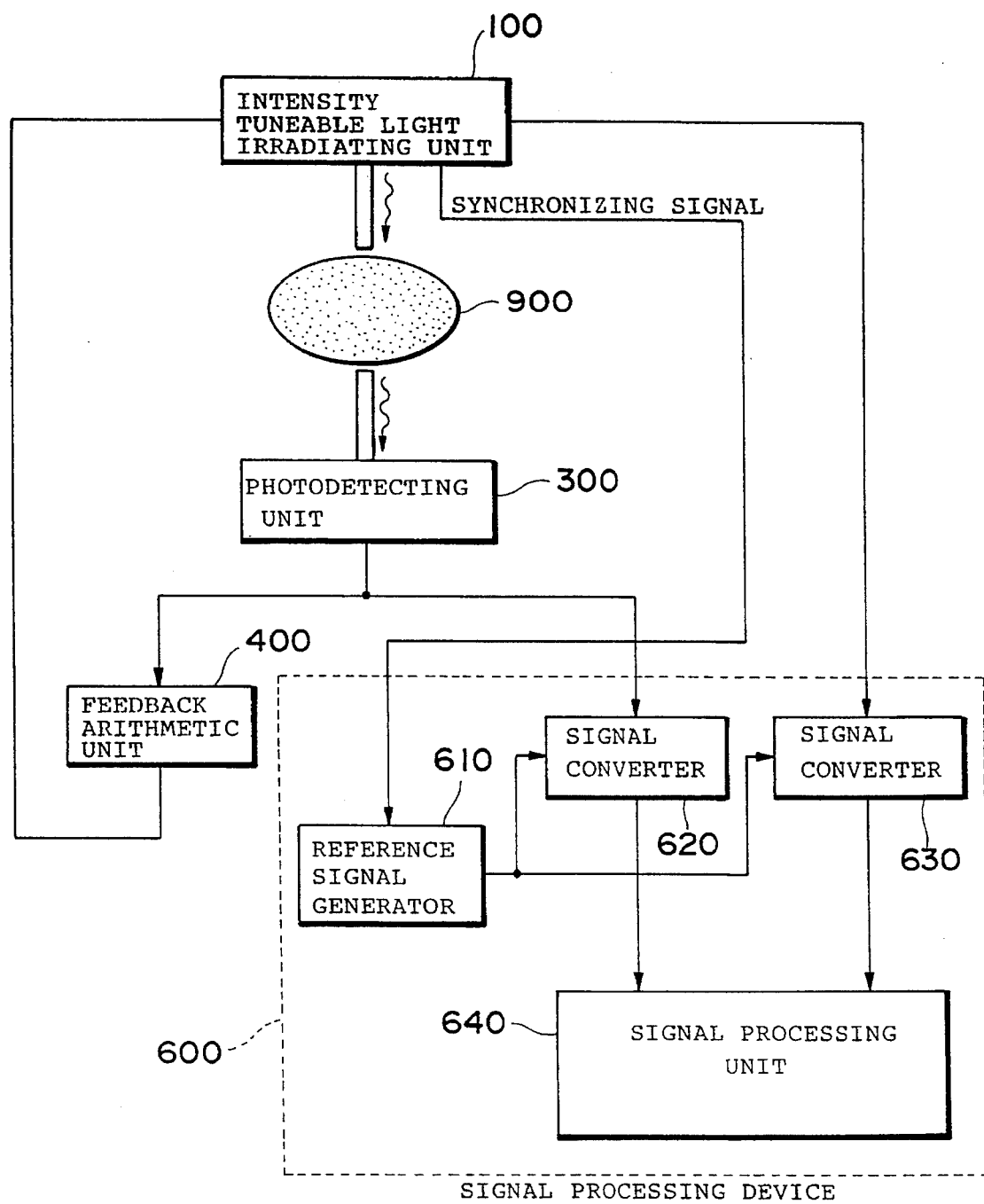
FIG. 9 is a block diagram of a photodetecting apparatus of the third embodiment of the present invention.

FIG. 9 is a block diagram of a photodetecting apparatus of the third embodiment of the present invention. The photodetecting apparatus of the present embodiment has the same configuration as the apparatus of the first embodiment except that a processing device 600 is different from the processing device 500 of the first embodiment.

The processing device 600 of the present embodiment comprises (1) a reference signal generator 610 for generating a reference signal having a reference frequency (f0) different from a modulation frequency (f1), (2) a signal converter 620 for receiving the reference signal and a modulating signal, calculating a product of both signals and thereafter generating a signal having a frequency difference ($\Delta f$) between the reference frequency and the modulation frequency, (3) a signal converter 630 for receiving the reference signal and an optically detected signal, calculating a product of both signals, and thereafter generating an signal having a frequency difference between the reference frequency and the modulation frequency, and (4) a signal processing unit 640 for obtaining a phase difference between the modulating signal and the optically detected signal based on an output signal waveform of the signal converter 620 and an output signal waveform of the signal converter 630.

Here, in order to make an output of an oscillator 120 in a intensity tuneable light irradiating unit 100 in synchronization with an output of the reference signal generator 610 in the processing device 600, a synchronizing signal is applied from the oscillator 120 to the reference signal generator 610 to control the output of the reference signal generator 610. As a result, phase fluctuation of the oscillator 120 and phase fluctuation of the reference signal generator 610, which are independent from each other, are adjusted, by which synchronization is attained and the measurement precision is improved. Note that an synchronizing signal may be applied from the reference signal generator 610 to the oscillator 120 to control the output of the oscillator 120.

Here, the signal converters 620 and 630 comprises a device, generally called double balanced mixer. Further, a lock-in amplifier is used in the measurement of phase difference in the signal processing unit 640.

The measurement of the phase difference with the photodetecting apparatus of the present embodiment is carried out in the same way as in the first embodiment until the intensity of the ac component of the optically detected signal generated from the photodetecting unit 300 substantially matches with the adjusting value. Thereafter, the processing device 600 receives the modulating signal and the optically detected signal and calculates a product of each signal and the reference frequency signal. The result of each calculation includes a signal component having a frequency $\Delta f$, and the signal component contains information of the phase difference between the modulating signal and the optically detected signal. The signal processing unit 640 receives two signals each having a frequency $\Delta f$ and obtains the phase difference between the modulating signal and the optically detected signal. The timing difference between the modulating signal and the optically detected signal can also be calculated from the results of the phase difference measurement.

(Fourth Embodiment)

The photodetecting apparatus of the present embodiment belongs to the first photodetecting apparatus of the present invention and is an apparatus to carry out the measurement successively with a plurality of measuring lights each having a different wavelength by selecting a measuring wavelength. Note that in the present embodiment, the case of two measuring lights, each having a different wavelength will be explained.

Figure 10:
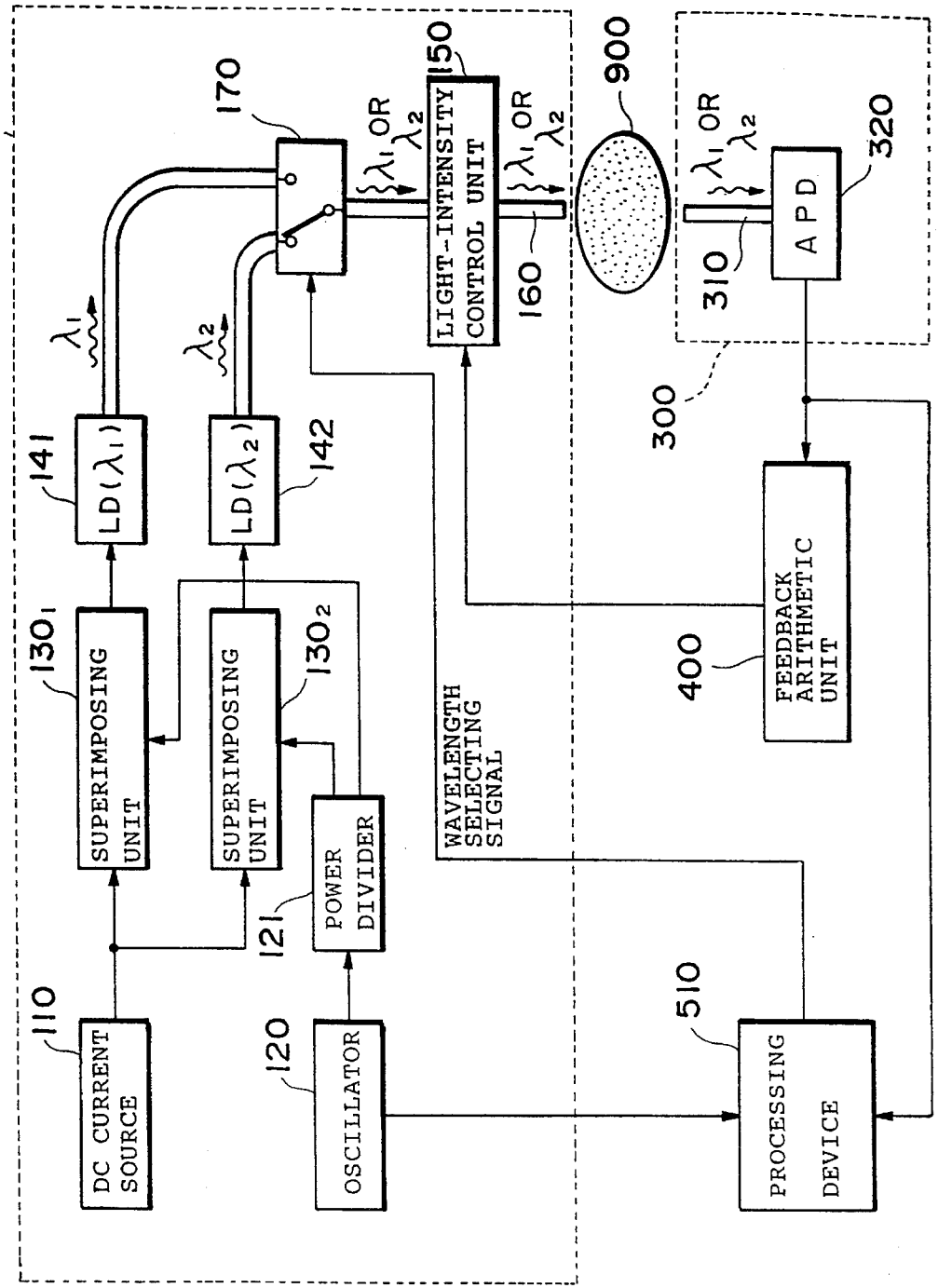
FIG. 10 is a block diagram of a photodetecting apparatus of the fourth embodiment of the present invention.

FIG. 10 is a block diagram of a photodetecting apparatus of the present embodiment. As shown in FIG. 10, this apparatus comprises (a) a intensity tuneable light irradiating unit 250 for selecting and emitting one of two kinds of lights to irradiate a scattering and absorption medium 900, each having a different wavelength, the intensity of which are modulated by a modulating signal having an ac component with a predetermined frequency in accordance with an external instruction, a quantity of generating light being adjustable by an external instruction, (b) a photodetecting unit 300 comprising an avalanche photodiode for detecting an optical signal having a predetermined frequency emerging from the scattering and absorption medium 900 after the optical signal is generated from intensity tuneable light irradiating unit 250, irradiates the scattering and absorption medium 900, and propagates therein, (c) a feedback arithmetic unit 400 for receiving an optically detected signal corresponding to an intensity of an optical signal emitted from the photodetecting-unit 300, sending an instruction to the intensity tuneable light irradiating unit 250 to increase the quantity of generating light when the intensity of the ac component of the optical signal detected by the photodetecting unit 300 is smaller than a predetermining value, and sending an instruction to the intensity tuneable light irradiating unit 250 to decrease the quantity of generating light when the intensity of the optical signal detected by the photodetecting unit 300 is larger than the predetermined value, and (d) a processing device 510 for receiving the modulating signal and the optically detected signal, obtaining a phase difference between the modulating signal and the optically detected signal, and sending an instruction to the intensity tuneable light irradiating unit 250 to select a wavelength.

Here, the intensity tuneable light irradiating unit 250 comprises (1) a dc current source 110 for supplying dc current, (2) an oscillator 120 for generating an ac signal having a modulation frequency, and a power divider 121 for outputting the ac signal generated from the oscillator 120 as two ac signals (3) a laser diode 141 for receiving a modulating signal generated from a superimposing unit 130$_1$ for superimposing one of the ac signals output from the power divider 121 on the dc current output from the dc current source 110, and emitting intensity-modulated light having a wavelength $\lambda_1$, (4) a laser diode 142 for receiving a modulating signal generated from a superimposing unit 130$_2$ for superimposing one of the ac signals output from the power divider 121 on the dc current output from the dc current source 110, and emitting intensity-modulated light having a wavelength $\lambda_2$, (5) a light selector 170 for selecting and emitting one of light emitted from the laser diode 141 and light emitted from the laser diode 142, (6) a light-intensity control unit 150 for receiving the light emitted from the light selector 170 and transmitting light with a transmittivity indicated from outside, and (7) an optical fiber cable 160 for guiding irradiation light emitted from the light-intensity control unit 150 to the surface of the scattering and absorption medium 900. Note that the superimposing unit 130$_1$ and the superimposing unit 130$_2$ have the same configurations as the superimposing unit 130 of the first embodiment.

The processing device 510 has a function to output a wavelength selecting signal to the light selector 170 to indicate a wavelength to be selected in addition to the functions of the processing device 500 of the first embodiment.

The measurement of the phase difference with the photodetecting apparatus of the present embodiment is carried out as follows.

First, the processing device 510 outputs a wavelength selecting signal to the light selector 170 in the intensity tuneable light irradiating unit 250 to select a wavelength $\lambda_1$ as a wavelength of measuring light. Thereafter, light the intensity of which is modulated to the initial intensity by a modulating signal having an ac component with a predetermined frequency and which is from the intensity tuneable light irradiating means 250 irradiates the scattering and absorption medium 900 which is an object to be measured. The ac component of the modulating signal is also applied to the processing device 510. The modulated light incident on the scattering and absorption medium 900 propagates in the scattering and absorption medium 900, emerges therefrom and is incident to the photodetecting unit 300. Thereafter, in the same manner as in the first embodiment, the phase difference between the modulating signal and the optically detected signal is obtained with the measuring light having a wavelength $\lambda_1$. The timing difference between the modulating signal and the optically detected signal can also be calculated from the results of the phase difference measurement.

Next, the processing device 510 outputs a wavelength selecting signal to the light selector 170 in the intensity tuneable light irradiating unit 250 to select a wavelength $\lambda_2$ as a wavelength of measuring light. Thereafter, in the same matter as the measuring light having the wavelength $\lambda_1$, the phase difference between the modulating signal and the optically detected signal is obtained with the measuring light having the wavelength $\lambda_2$.

Note that in the present embodiment, the case of two wavelengths of measuring lights is shown, but if the number of outputs of the power divider and the number of wavelengths of measuring light are more than three, the number of pairs of the superimposing unit and the laser diode is adjusted with respect to the number of wavelengths, by which the same configuration as in the present embodiment will be attained.

(Fifth Embodiment)

The photodetecting apparatus of the present embodiment, in the same way as the fourth embodiment, belongs to the first photodetecting apparatus of the present invention and is an apparatus to carry out the measurement successively with a plurality of measuring lights each having a different wavelength by selecting a measuring wavelength. Note that in the present embodiment, the case of two measuring lights, each having a different wavelength will be explained.

Figure 11:
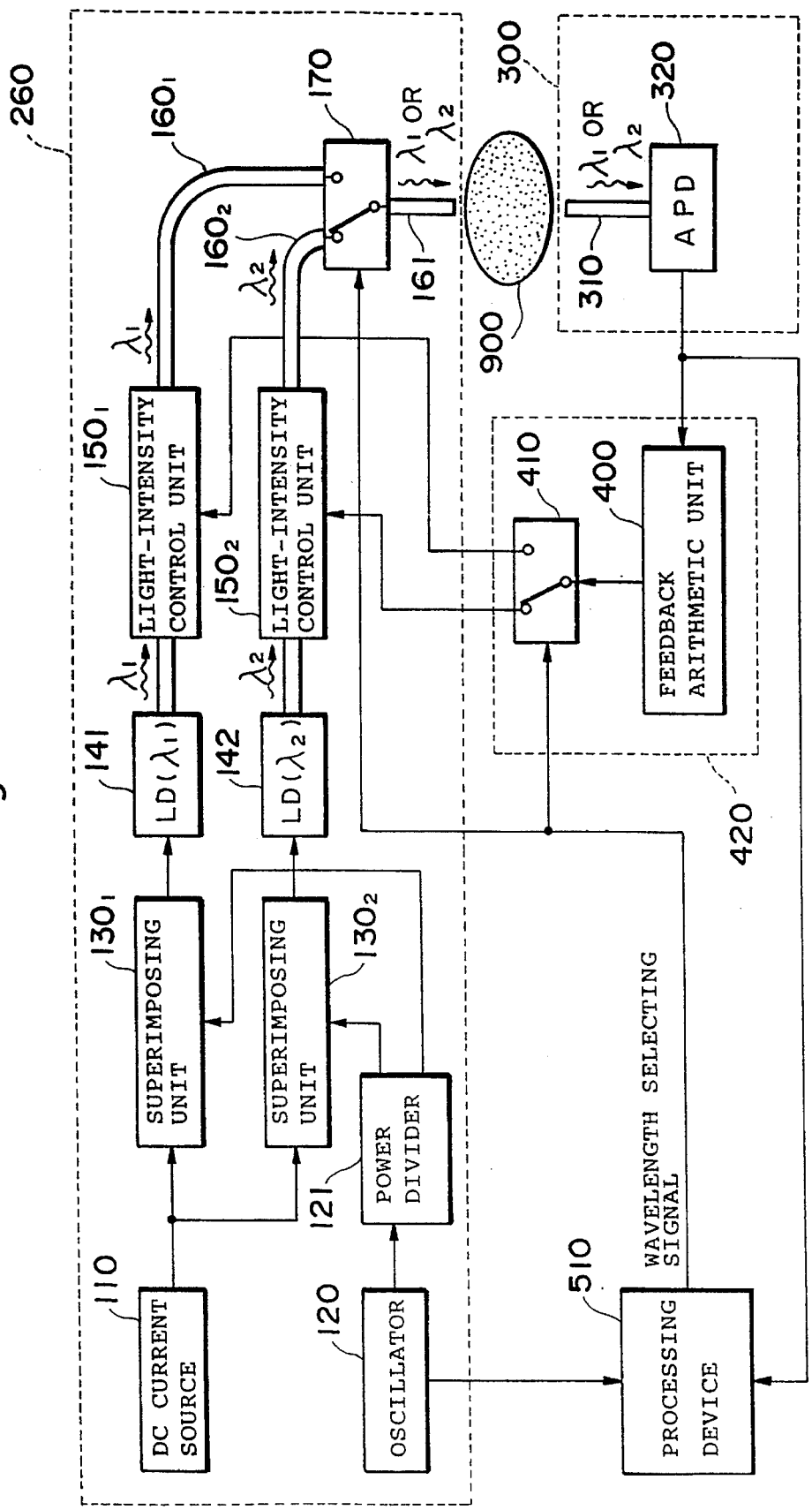
FIG. 11 is a block diagram of a photodetecting apparatus of the fifth embodiment of the present invention.

FIG. 11 is a block diagram of a photodetecting apparatus of the present embodiment. As shown in FIG. 11, this apparatus comprises (a) a intensity tuneable light irradiating unit 260 for selecting and emitting one of two kinds of lights to irradiate a scattering and absorption medium 900, each having a different wavelength, the intensity of which are modulated by a modulating signal having an ac component with a predetermined frequency in accordance with an external instruction, a quantity of generating light being adjustable by an external instruction, (b) a photodetecting unit 300 comprising an avalanche photodiode for detecting an optical signal having a predetermined frequency emerging from the scattering and absorption medium 900 after the optical signal is generated from intensity tuneable light irradiating unit 260, irradiates the scattering and absorption medium 900, and propagates therein, (c) a feedback unit 420 for receiving an optically detected signal corresponding to an intensity of an optical signal emitted from the photodetecting unit 300, calculating increase of the quantity of generating light of the intensity tuneable light irradiating unit 260 when the intensity of the ac component of the optical signal detected by the photodetecting unit 300 is smaller than a predetermined value, and calculating decrease of the quantity of generating light of the intensity tuneable light irradiating unit 260 when the intensity of the optical signal detected by the photodetecting unit 300 is larger than the predetermined value, and receiving the instruction of wavelength selection made on the intensity tuneable light irradiating unit 260 and referring to this instruction, sending an indication of a quantity of generating light for the intensity tuneable light irradiating unit 260 to a passage corresponding to the instruction of wavelength selection, and (d) a processing device 510 for receiving a modulating signal and an optically detected signal, obtaining a phase difference between the modulating signal and the optically detected signal, and sending an instruction of wavelength selection to the intensity tuneable light irradiating unit 260 and the feedback unit 420.

Here, the intensity tuneable light irradiating unit 260 comprises (1) a dc current source 110 for supplying dc current, (2) an oscillator 120 for generating an ac signal having a modulation frequency, and a power divider 121 for outputting the ac signal generated from the oscillator 120 as two ac signals, (3) a laser diode 141 for receiving a modulating signal generated from a superimposing unit 130₁ for superimposing one of the ac signals output from the power divider 121 on the dc current output from the dc current source 110, and emitting intensity-modulated light having a wavelength $\lambda_1$, and a light-intensity control unit 150₁ for receiving light emitted from the laser diode 141 and transmitting light at a transmittivity indicated from outside, (4) a laser diode 142 for receiving a modulating signal generated from a superimposing unit 130₂ for superimposing one of the ac signals output from the power divider 121 on the dc current output from the dc current source 110, and emitting intensity-modulated light having a wavelength $\lambda_2$, and a light-intensity control unit 150₂ for receiving light emitted from the laser diode 142 and transmitting light at a transmittivity indicated from outside,(5) a light selector 170 for selecting and emitting one of light emitted from the light-intensity control unit 150₁ and light emitted from the light-intensity control unit 150₂, and (6) an optical fiber cable 161 for guiding irradiation light emitted from the light selector 170 to the surface of the scattering and absorption medium 900. Note that the light-intensity control unit 150₁ and the light-intensity control unit 150₂ have the same configurations as the light-intensity control unit 150 of the first embodiment.

The feedback unit 420 comprises (1) a feedback arithmetic unit 400, and (2) a passage selector 410 for receiving a wavelength selecting signal output from the processing device 510, and selecting a unit to which the indication of the quantity of light generated from the feedback arithmetic unit 400 is sent in accordance with the selected measuring wavelength.

The measurement of the phase difference with the photodetecting apparatus of the present embodiment is carried out as follows.

First, the processing device 510 outputs a wavelength selecting signal to the light selector 170 in the intensity tuneable light irradiating unit 260 and a passage selector in the feedback unit 420 to select a wavelength $\lambda_1$ as a wavelength of measuring light. Thereafter, light having a wavelength $\lambda_1$ the intensity of which is modulated to the initial intensity by a modulating signal having an ac component with a predetermined frequency and which is from the intensity tuneable light irradiating means 260 irradiates the scattering and absorption medium 900 which is an object to be measured. The ac component of the modulation frequency is also applied to the processing device 510. The modulated light incident on the scattering and absorption medium 900 propagates in the scattering and absorption medium 900, emerges therefrom and is incident to the photodetecting unit 300. Thereafter, in the same manner as in the fourth embodiment, the phase difference between the modulating signal and the optically detected signal is obtained with the measuring light having a wavelength $\lambda_1$.

Next, the processing device 510 outputs a wavelength selecting signal to the light selector 170 in the intensity tuneable light irradiating unit 260 to select a wavelength $\lambda_2$ as a wavelength of measuring light. Thereafter, in the same matter as the measuring light having the wavelength $\lambda_1$, the phase difference between the modulating signal and the optically detected signal is obtained with the measuring light having the wavelength $\lambda_2$.

Note that the timing difference between the modulating signal and the optically detected signal can also be calculated from the results of the phase difference measurement.

Further, similar to the fourth embodiment, if the number of outputs of the power divider and the number of wavelengths of measuring lights are more than three, the number of groups of the superimposing unit, the laser diode and the light-intensity control unit is adjusted with respect to the number of wavelengths, by which the same configuration as in the present embodiment will be attained.

(Sixth Embodiment)

The photodetecting apparatus of the present embodiment, in the same way as the fifth embodiment, belongs to the first photodetecting apparatus of the present invention and is an apparatus to carry out the measurement successively with a plurality of measuring lights each having a different wavelength by selecting a measuring wavelength. Note that in the present embodiment, the case of two measuring lights, each having a different wavelength will be explained.

Figure 12:
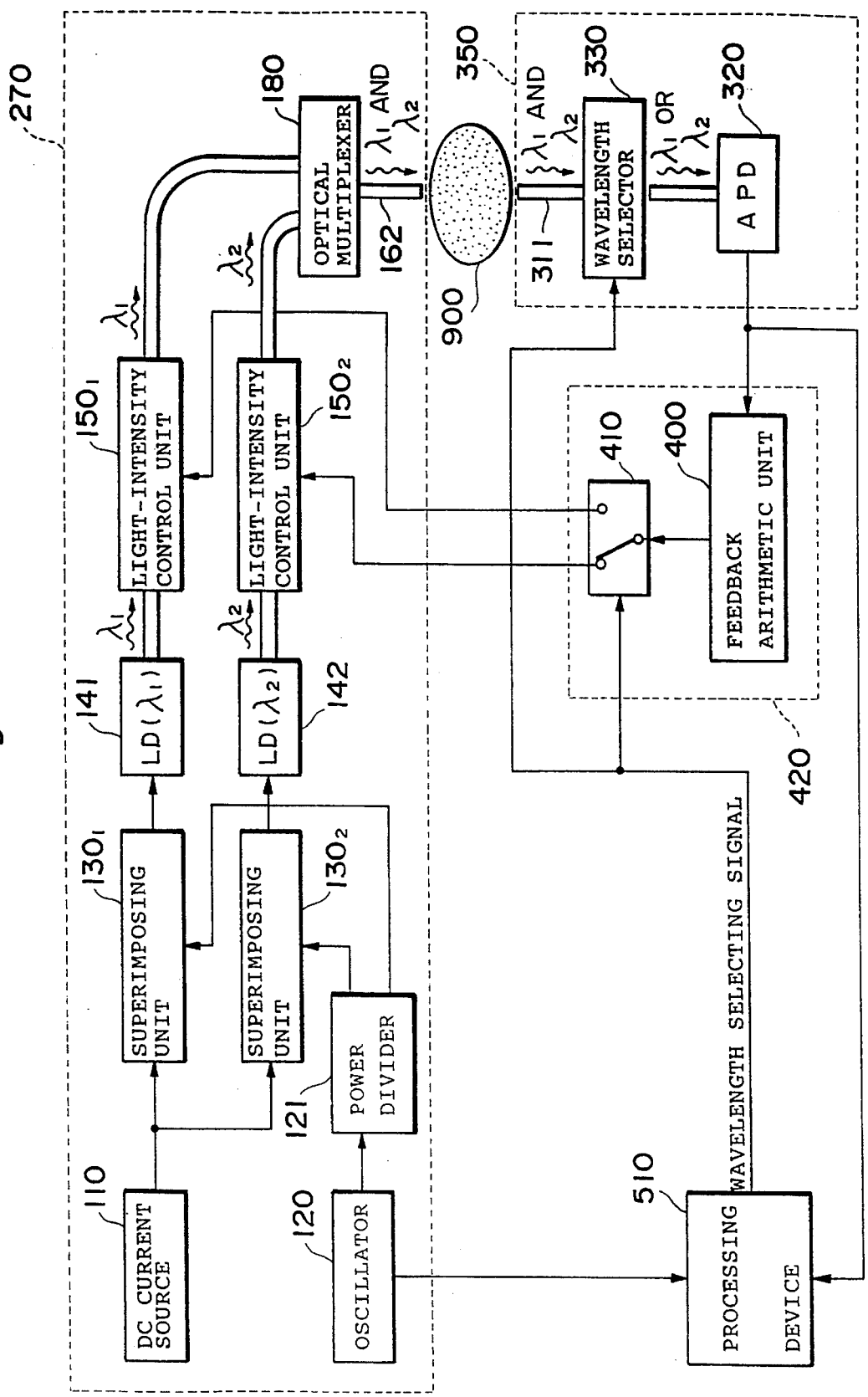
FIG. 12 is a block diagram of a photodetecting apparatus of the sixth embodiment of the present invention.

FIG. 12 is a block diagram of a photodetecting apparatus of the present embodiment. As shown in FIG. 12, this apparatus comprises (a) a intensity tuneable light irradiating unit 270 for emitting two kinds of lights to irradiate a scattering and absorption medium 900, each having a different wavelength, the intensity of which are modulated by a modulating signal having an ac component with a predetermined frequency in accordance with an external instruction, a quantity of generating light being adjustable by an external instruction, (b) a photodetecting unit 350 for selecting light having a wavelength indicated from an outside among optical signals each having a predetermined frequency emerging from the scattering and absorption medium 900 after the optical signal is generated from intensity tuneable light irradiating unit 270, irradiates the scattering and absorption medium 900, and propagates therein, (c) a feedback unit 420 for receiving an optically detected signal corresponding to an intensity of an optical signal emitted from the photodetecting unit 320, calculating increase of the quantity of generating light of the intensity tuneable light irradiating unit 270 when the intensity of the ac component of the optical signal detected by the photodetecting unit 320 is smaller than a predetermined value, and calculating decrease of the quantity of generating light of the intensity tuneable light irradiating unit 270 when the intensity of the optical signal detected by the photodetecting unit 320 is larger than the predetermined value, and receiving the instruction of wavelength selection made on the intensity tuneable light irradiating unit 270 and referring to this instruction, sending an indication of a quantity of generating light for the intensity tuneable light irradiating unit 270 to a passage corresponding to the instruction of wavelength selection, and (d) a processing device 510 for receiving a modulating signal and an optically detected signal, obtaining a phase difference between the modulating signal and the optically detected signal, and sending an instruction of wavelength selection to the intensity tuneable light irradiating unit 270 and the feedback unit 420.

Here, the intensity tuneable light irradiating unit 270 comprises (1) a dc current source 110 for supplying dc current, (2) an oscillator 120 for generating an ac signal having a modulation frequency, and a power divider 121 for outputting the ac signal generated from the oscillator 120 as two ac signals, (3) a laser diode 141 for receiving a modulating signal generated from a superimposing unit $130_1$ for superimposing one of the ac signals output from the power divider 121 on the dc current output from the dc current source 110, and emitting intensity-modulated light having a wavelength $\lambda_1$, and a light-intensity control unit $150_1$ for receiving light emitted from the laser diode 141 and transmitting light at a transmittivity indicated from outside, (4) a laser diode 142 for receiving a modulating signal generated from a superimposing unit $130_2$ for superimposing one of the ac signals output from the power divider 121 on the dc current output from the dc current source 110, and emitting intensity-modulated light having a wavelength $\lambda_2$, and a light-intensity control unit $150_2$ for receiving light emitted from the laser diode 142 and transmitting light at a transmittivity indicated from outside,(5) an optical multiplexer 180 for coupling light emitted from the light-intensity control unit $150_1$ and light emitted from the light-intensity control unit $150_2$, and (6) an optical fiber cable 162 for guiding irradiation light emitted from the optical multiplexer 180 to the surface of the scattering and absorption medium 900.

The photodetecting unit 350 comprises (1) an optical fiber cable 311 for receiving an optical signal emerging from the scattering and absorption medium 900, (2) a wavelength selector 330 for receiving an optical signal emerging from the optical fiber cable 311, and emitting light with a wavelength indicated by the processing device 510, and (3) an avalanche photodiode 320 for receiving light emitted from the wavelength selector 330 and converting the light into an electric signal.

The measurement of the phase difference with the photodetecting apparatus of the present embodiment is carried out as follows.

First, the processing device 510 outputs a wavelength selecting signal to the wavelength selector 330 in the photodetecting unit 350 and a passage selector in the feedback unit 420 to select a wavelength $\lambda_1$ as a wavelength of measuring light and sends this signal. Thereafter, light having wavelengths $\lambda_1$ and $\lambda_2$ the intensity of which are modulated to the initial intensity by a modulating signal having an ac component with a predetermined frequency and which is from the intensity tuneable light irradiating means 270 irradiates the scattering and absorption medium 900 which is an object to be measured. The modulating signal is also applied to the processing device 510. The modulated light incident on the scattering and absorption medium 900 propagates in the scattering and absorption medium 900, emerges therefrom and is incident to the photodetecting unit 350. The photodetecting unit 350 selects light having a wavelength $\lambda_1$ by the wavelength selector 330, and thereafter detects light having a wavelength $\lambda_1$ by the avalanche photodiode 320 and outputs the optically detected signal. Thereafter, in the same manner as in the fifth embodiment, the phase difference between the modulating signal and the optically detected signal is obtained with the measuring light having a wavelength $\lambda_1$.

Next, the processing device 510 outputs a wavelength selecting signal to the wavelength selector 330 in the intensity tuneable light irradiating unit 350 and the passage selector in the feedback unit 420 to select a wavelength $\lambda_2$ as a wavelength of measuring light. Thereafter, in the same matter as the measuring light having the wavelength $\lambda_1$, the phase difference between the modulating signal and the optically detected signal is obtained with the measuring light having the wavelength $\lambda_2$.

Note that similar to the first embodiment, the timing difference between the modulating signal and the optically detected signal can also be calculated from the results of the phase difference measurement.

Further, similar to the fourth embodiment, if the number of wavelengths of measuring light is more than three, the number of groups of the number of branches of the power divider, the superimposing unit, the laser diode and the light-intensity control unit is adjusted with respect to the number of wavelengths, by which the same configuration as in the present embodiment will be attained.

(Seventh Embodiment)

The photodetecting apparatus of the present embodiment, in the same way as the fifth embodiment, belongs to the first photodetecting apparatus of the present invention and is an apparatus to carry out the measurement successively with a plurality of measuring lights each having a different wavelength by selecting a measuring wavelength. The apparatus of the present embodiment is that modification made to the first embodiment in the second embodiment is made to the fifth embodiment or the sixth embodiment. Note that in the present embodiment, the case of two measuring lights, each having a different wavelength will be explained.

Figure 13:
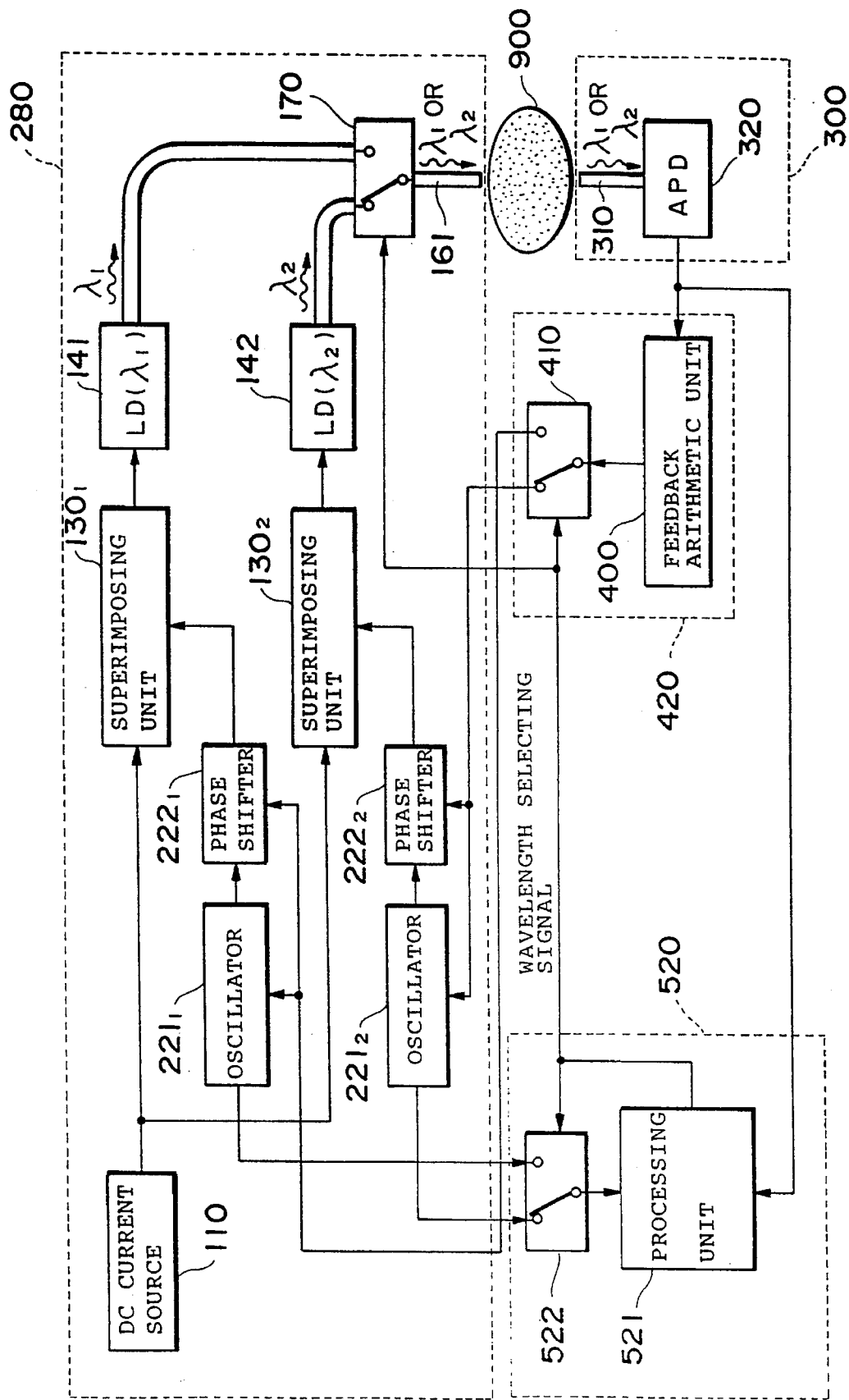
FIG. 13 is a block diagram of a photodetecting apparatus of the seventh embodiment of the present invention.

FIG. 13 is a block diagram of a photodetecting apparatus of the present embodiment. As shown in FIG. 13, this apparatus comprises (a) a intensity tuneable light irradiating unit 280 for selecting and emitting one of two,kinds of lights to irradiate a scattering and absorption medium 900, each having a different wavelength, the intensity of which are modulated by a modulating signal having an ac component with a predetermined frequency in accordance with an external instruction, a quantity of generating light being adjustable by an external instruction, (b) a photodetecting unit 300 comprising an avalanche photodiode for detecting an optical signal having a predetermined frequency emerging from the scattering and absorption medium 900 after the optical signal is generated from intensity tuneable light irradiating unit 280, irradiates the scattering and absorption medium 900, and propagates therein, (c) a feedback unit 420 for receiving an optically detected signal corresponding to an intensity of an optical signal emitted from the photodetecting unit 300, calculating increase of the quantity of generating light of the intensity tuneable light irradiating unit 280 when the intensity of the ac component of the optical signal detected by the photodetecting unit 300 is smaller than a predetermined value, and calculating decrease of the quantity of generating light of the intensity tuneable light irradiating unit 280 when the intensity of the optical signal detected by the photodetecting unit 300 is larger than the predetermined value, and receiving the instruction of wavelength selection made on the intensity tuneable light irradiating unit 280 and referring to this instruction, sending an indication of a quantity of generating light for the intensity tuneable light irradiating unit 280 to a passage corresponding to the instruction of wavelength selection, and (d) a processing device 520 for receiving a modulating signal and an optically detected signal, obtaining a phase difference between the modulating signal and the optically detected signal, and sending an instruction to the intensity tuneable light irradiating unit 280 and the feedback unit 420 to select a wavelength.

Here, the intensity tuneable light irradiating unit 280 comprises (1) a dc current source 110 for supplying dc current, (2) an oscillator 221₁ for generating an ac signal having a modulation frequency of modulation to be made on light having a wavelength $\lambda_1$ and an amplitude controlled in accordance with the external instruction, a phase shifter 222₁ for receiving an ac signal generated from the oscillator 221₁ and compensating a variation of phase due to the amplitude of the signal generated from the oscillator 221₁ by controlling an amount of variation of the phase in accordance with the external instruction, a superimposing unit 130₁ for superimposing the ac signal emitted from the phase shifter 222₁ on the dc current generated from the dc current source 110, and a laser diode 141 for receiving the modulating signal emitted from the superimposing unit 130₁ and emitting intensity-modulated light having a wavelength $\lambda_1$, (3) an oscillator 221₂ for generating an ac signal having a modulation frequency of modulation to be made on light having a wavelength $\lambda_2$ and an amplitude controlled in accordance with the external instruction, a phase shifter 222₂ for receiving an ac signal generated from the oscillator 221₂ and compensating a variation of phase due to the amplitude of the signal generated from the oscillator 221₂ by controlling an amount of variation of the phase in accordance with the external instruction, a superimposing unit 130₂ for superimposing the ac signal emitted from the phase shifter 222₂ on the dc current generated from the dc current source 110, and a laser diode 142 for receiving the modulating signal output from the superimposing unit 130₂ and emitting intensity-modulated light having a wavelength $\lambda_2$, (4) a light selector 170 for selecting and emitting one of light emitted from the laser diode 141 and light emitted from the laser diode 142, and (5) an optical fiber cable 161 for guiding irradiation light emitted from the light selector 170 to the surface of the scattering and absorption medium 900.

The processing device 520 comprises (1) a processing unit 521 having the same function as the processing device 510 of the fifth embodiment, and (2) a selector 522 for receiving a wavelength selecting signal output from the processing unit 521 and selecting and emitting a modulating signal with respect to light having the selected measuring wavelength.

The measurement of the phase difference with the photodetecting apparatus of the present embodiment is carried out as follows.

First, the processing unit 521 outputs a wavelength selecting signal to the light selector 170 in the intensity tuneable light irradiating unit 280 and a passage selector 410 in the feedback unit 420 to select a wavelength $\lambda_1$ as a wavelength of measuring light and sends this signal. Thereafter, light having a wavelength $\lambda_1$ the intensity of which is modulated to the initial intensity by a modulating signal having an ac component with a predetermined frequency and which is from the intensity tuneable light irradiating means 280 irradiates the scattering and absorption medium 900 which is an object to be measured. The ac component of the modulation frequency is also applied to the processing device 521. The modulated light incident on the scattering and absorption medium 900 propagates in the scattering and absorption medium 900, emerges therefrom and is incident to the photodetecting unit 300. Thereafter, in the same manner as in the second embodiment, the phase difference between the modulating signal and the optically detected signal is obtained with the measuring light having a wavelength $\lambda_1$.

Next, the processing device 521 outputs a wavelength selecting signal to the light selector 170 in the intensity tuneable light irradiating unit 280 and the passage selector 410 in the feedback unit 420 to select a wavelength $\lambda_2$ as a wavelength of measuring light. Thereafter, in the same matter as the measuring light having the wavelength $\lambda_1$, the phase difference between the modulating signal and the optically detected signal is obtained with the measuring light having the wavelength $\lambda_2$.

Note that similar to the first embodiment, the timing difference between the modulating signal and the optically detected signal can also be calculated from the results of the phase difference measurement.

Further, similar to the fourth embodiment, if the number of wavelengths of measuring light is more than three, the number of groups of the number of branches of the power divider, the superimposing unit, the laser diode and the light-intensity control unit is adjusted with respect to the number of wavelengths, by which the same configuration as in the present embodiment will be attained.

(Eighth Embodiment)

The photodetecting apparatus of the present embodiment belongs to the second photodetecting apparatus of the present invention and is an apparatus to carry out the measurement with a plurality of measuring lights each having a different wavelength at once.

Figure 14:
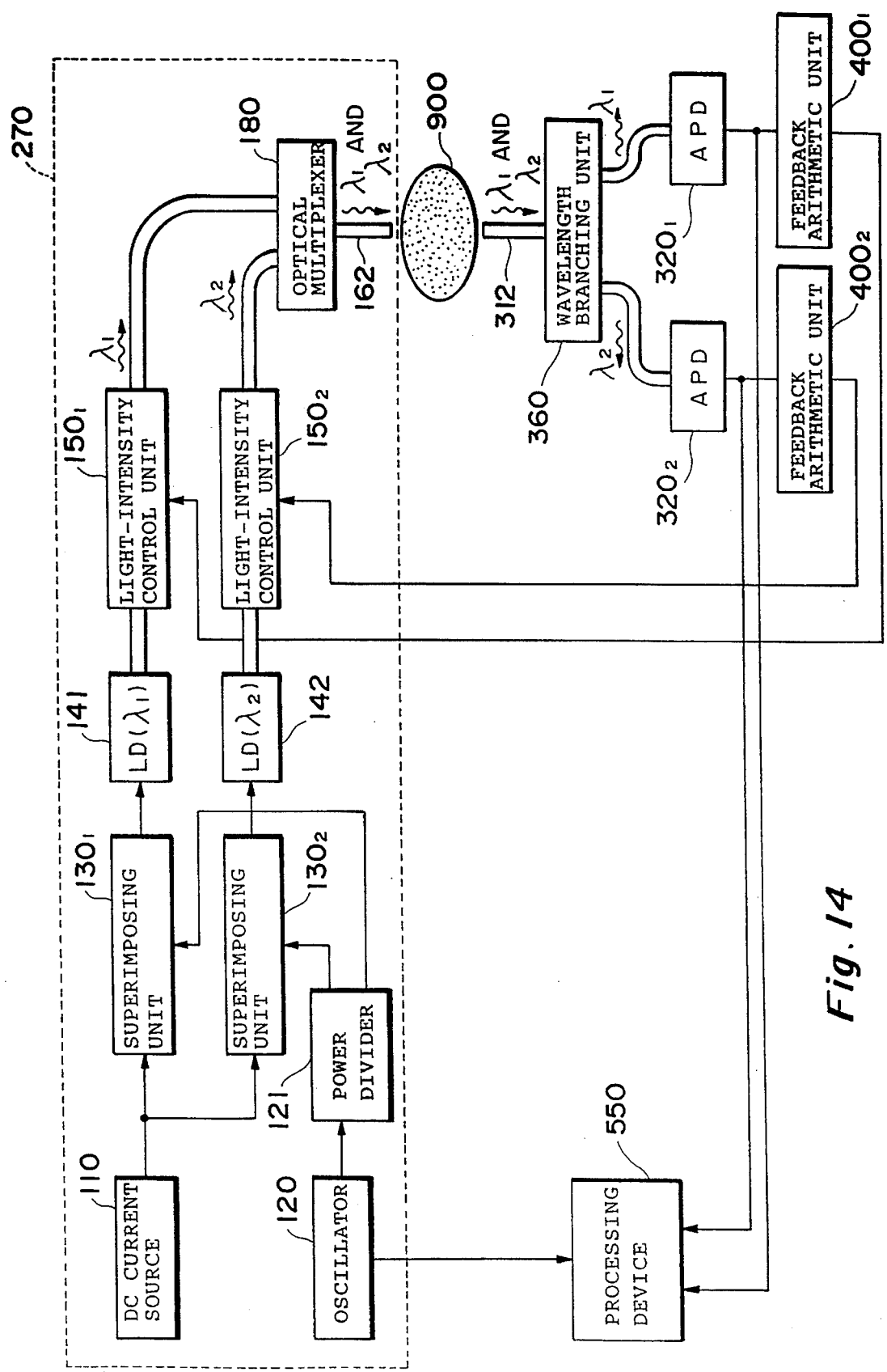
FIG. 14 is a block diagram of a photodetecting apparatus of the eighth embodiment of the present invention.

FIG. 14 is a block diagram of a photodetecting apparatus of the present embodiment. The apparatus of the present embodiment carries out the same prior setting of the apparatus and the actual measurement corresponding to one wavelength as the apparatus of the first embodiment but the light incidence on a scattering and absorption medium which is an object to be measured and detection of light emerging from the scattering and absorption medium are carried out for all wavelengths at once.

As shown in FIG. 14, this apparatus of the present embodiment comprises (a) a intensity tuneable light irradiating unit 270 for emitting two kinds of lights (wavelength= $\lambda_1$ and $\lambda_2$) to irradiate a scattering and absorption medium 900, each having a different wavelength, the intensity of which are modulated by a modulating signal having an ac component with a predetermined frequency, a quantity of generating light being adjustable in accordance with an external instruction, (b) a wavelength branching unit 360 for receiving an optical signal having a predetermined wavelength emerging from the scattering and absorption medium 900 after the optical signal is generated from intensity tuneable light irradiating unit 270, irradiates the scattering and absorption medium 900 and propagates in the scattering and absorption medium 900, and selecting and emitting light having a wavelength $\lambda_1$ and light having a wavelength $\lambda_2$ separately, (c) an avalanche photodiode (APD) 320₁ for detecting light having a wavelength $\lambda_1$ emitted from the wavelength branching unit 360, (d) a feedback arithmetic unit 400₁ for sending an instruction to the intensity tuneable light irradiating unit 270 to increase a quantity of generating light having a wavelength $\lambda_1$ when the intensity of the ac component of the optical signal detected by the photodetecting unit 320₁ is smaller than a predetermined value, and sending an instruction to the intensity tuneable light irradiating unit 270 to decrease the quantity of generating light having a wavelength $\lambda_1$ when the intensity of the optical signal detected by the photodetecting unit 320₁ is larger than the predetermined value, (e) an avalanche photodiode (APD) 320₂ for detecting light having a wavelength $\lambda_2$ emitted from the wavelength branching unit 360, (f) a feedback arithmetic unit 400₂ for sending an instruction to the intensity tuneable light irradiating unit 270 to increase a quantity of generating light having a wavelength $\lambda_2$ when the intensity of the ac component of the optical signal detected by the photodetecting unit 320₂ is smaller than the predetermined value, and sending an instruction to the intensity tuneable light irradiating unit 270 to decrease the quantity of generating light having a wavelength $\lambda_2$ when the intensity of the optical signal detected by the photodetecting unit 320₂ is larger than the predetermined value, and (g) a processing device 550 for receiving a modulating signal and an optically detected signal for each wavelength of measuring light, and obtaining a phase difference between the modulating signal and the optically detected signal, for each wavelength of measuring light.

Here, the APDs 320₁ and 320₂ have the same configuration as the APD 320 of the first embodiment, and the feedback arithmetic units 400₁ and 400₂ have the same configuration as the feedback arithmetic unit 400 of the first embodiment.

The measurement of the phase difference with the photodetecting apparatus of the present embodiment is carried out as follows.

Prior to the measurement, the gain of the APD 320₁ and 320₂ is determined and the bias voltage to be this gain is applied to the APDs 320₁ and 320₂. Then, with this gain, the time between the light input and the output of the optically detected signal in the APDs 320₁ and 320₂ is measured and stored in the processing device 550. At the same time, an adjusting value for the intensity of the ac component of the optically detected signal is determined, and the reference voltage is set by adjusting the variable dc voltage source in the feedback arithmetic units 400₁ and 400₂. After these preparation, the photodetecting operation to obtain the phase difference is started.

First, light having wavelengths $\lambda_1$ and $\lambda_2$ the intensity of which is modulated to the initial intensity by a modulating signal having an ac component with a predetermined frequency and which is from the intensity tuneable light irradiating means 270 irradiates the scattering and absorption medium 900 which is an object to be measured. The modulating signal is also applied to the processing device 550. The modulated light incident on the scattering and absorption medium 900 propagates in the scattering and absorption medium 900, emerges therefrom and is incident to the wavelength branching unit 360. Then, the modulated light is branched into light having a wavelength $\lambda_1$ and light having a wavelength $\lambda_2$.

The light having a wavelength $\lambda_1$ is incident on the APD 320₁ and converted into an electric signal (current signal), and thereafter it is emitted as an optically detected signal. The optically detected signal emitted from the APD 320₁ is sent to the feedback arithmetic unit 400₁ and the processing device 550.

The feedback arithmetic unit 400₁ extracts the ac component from the input optically detected signal. If the intensity of the ac electric signal is smaller than the adjusting value, the feedback arithmetic unit $400_1$ sends an instruction to the light-intensity control unit $150_1$ in the intensity tuneable light irradiating unit 270 to increase a quantity of transmitting light, and if the intensity of the ac electric signal is larger than the adjusting value, it sends an instruction to the light-intensity control unit $150_1$ to decrease the quantity of transmitting light. The intensity of output light having a wavelength $\lambda_1$ from the intensity tuneable light irradiating unit 270 is controlled with operations in the feedback loop of the intensity tuneable light irradiating unit 270—the APD $320_1$—the feedback arithmetic unit $400_1$—the intensity tuneable light irradiating unit 270. Then, as the gain of the APD $320_1$ is fixed, the intensity of the ac component having a modulation frequency emitted from the APD $320_1$ is maintained so as to substantially match with the preset adjusting value.

After the intensity of the ac component of the optically detected signal emitted from the APD $320_1$ substantially matches with the adjusting value, the processing device 550 processes the ac component of the modulating signal and the ac component of the optically detecting signal to obtain the phase difference between the modulating signal and the optically detected signal.

At the same time as the measurement with light having a wavelength $\lambda_1$, the measurement with light having a wavelength $\lambda_2$ is carried out in the same way as the measurement with light having a wavelength $\lambda_1$. Note that the feedback loop formed in measurement with light having a wavelength $\lambda_2$ is a loop of the variable quantity of light irradiating unit 270 (light-intensity control unit $150_2$)—the APD $320_2$—the feedback arithmetic unit $400_2$—the intensity tuneable light irradiating unit 270 (light-intensity control unit $150_2$).

Note that similar to the first embodiment, the timing difference between the modulating signal and the optically detected signal can also be calculated from the results of the phase difference measurement.

Further, if the number of wavelengths of measuring light are more than three, the number of groups of the superimposing unit, the laser diode and the light-intensity control unit, specification of the optical multiplexer, specification of the wavelength branching unit, and the number of pairs of the APD and the feedback arithmetic unit are adjusted with respect to the number of wavelengths, by which the same configuration as in the present embodiment will be attained.

The modification made on the first embodiment in the second embodiment and the third embodiment can pe applied to the present embodiment, which also shows the same effects.

The present invention is not limited to the above embodiment but can be modified in many ways.

For example, a photomultiplier tube, a photo tube, a photodiode, a pin photodiode or an electron-implantation APD built-in photomultiplier tube can be used as a photodetecting unit, which can also obtain the same effects.

Further, for the measurement with light having a plurality of wavelengths with the apparatus of the first to third embodiments, a tuneable laser device can be employed to use a desired wavelength. Further, the number of frequency components included in the ac component of the modulating signal is not limited to one but can be plural. In the case of a plurality of frequency components, a plurality of frequency selecting filters corresponding to each frequency component need to be prepared upon the light incidence on the photodetecting unit, and for each frequency which is an object to be measured, the frequency selecting filter is switched, or the frequency components need to be separated in the processing device.

Furthermore, an irradiation/non-irradiation function can be added to the intensity tuneable light irradiating unit, and then generating irradiation light is pulse-like light.

Thus, as described above, according to the photodetecting apparatus of the present invention, because the gain of the photodetecting unit is fixed, and the intensity of the intensity-modulated light to irradiate the scattering and absorption medium is an object of the feedback control for making the intensity of the ac component of the optically detected signal emitted from the photodetecting unit to be fixed, time between the light incident on the photodetecting unit and the output of the optically detected signal is substantially constant, and a signal with a level which is easily handled can be obtained. Then, the phase difference between the optical signal the intensity of which is modulated and which irradiates the scattering and absorption medium and the optical signal emerging through the scattering and absorption medium can be measured easily with high precision.

From the invention thus described, it will be obvious that the invention may be varied in many ways. Such variations are not to be regarded as a departure from the spirit and scope of the invention, and all such modifications as would be obvious to one skilled in the art are intended to be included within the scope of the following claims.

The basic Japanese Application No. 5-304311 filed on Dec. 3, 1993 is hereby incorporated by reference.

What is claimed is:

1. A photodetecting apparatus comprising:

intensity tuneable light irradiating means for generating light to irradiate a scattering and absorption medium, an intensity of said light being modulated by a modulating signal having an ac component with a predetermined frequency, an amount of modulation of generating light or a quantity of generating light being adjustable in accordance with an external instruction;

photodetecting means for detecting an optical signal having a component with said predetermined frequency emerging from said scattering and absorption medium after said optical signal is generated from said intensity tuneable light irradiating means, irradiates said scattering and absorption medium and propagates in said scattering and absorption medium;

feedback means for receiving an optically detected signal corresponding to the intensity of said optical signal emitted from said photodetecting means, sending an instruction to said intensity tuneable light irradiating means to increase the quantity of generating light or to increase the amount of modulation of generating light when the intensity of an ac component of said optically detected signal detected by said photodetecting means is smaller than a predetermined value, and sending an instruction to said intensity tuneable light irradiating means to decrease the quantity of generating light or to decrease the amount of modulation of generating light when the intensity of the ac component of said optically detected signal detected by said photodetecting means is larger than the predetermined value; and processing means for receiving said modulating signal and said optically detected signal and obtaining one of a timing difference between said modulating signal and said optically detected signal, and a phase difference between said modulating signal and said optically detected signal.

2. An photodetecting apparatus according to claim 1, wherein said modulating signal is formed by superimposing one or more kinds of frequency components on a dc component.

3. An photodetecting apparatus according to claim 1, wherein light generated from said intensity tuneable light irradiating means is pulsed light.

4. An photodetecting apparatus according to claim 1, wherein said intensity tuneable light irradiating means comprises a modulating signal generating unit for generating said modulating signal on which said ac component with said predetermined frequency is superimposed;

light source means for receiving said modulating signal, and generating light the intensity of which is modulated by said predetermined frequency; and a light transmittivity varying unit for varying light transmittivity in accordance with a quantity-of-irradiation-light indicating signal sent from said feedback means.

5. A photodetecting apparatus according to claim 1, wherein said intensity tuneable light irradiating means comprises a modulating signal generating unit for generating said modulating signal on which said ac component with said predetermined frequency is superimposed and which has an amplitude corresponding to a quantity-of-irradiation-light indicating signal sent from said feedback means; and light source means for receiving said modulating signal and generating light the intensity of which is modulated by said predetermined frequency.

6. A photodetecting apparatus according to claim 4, wherein said light source means comprises a light emitting unit for generating light having a variable wavelength.

7. A photodetecting apparatus according to claim 4, wherein said light source means comprises a plurality of light emitting units, each generating light having a different wavelength; and a light selecting unit for selecting and taking out one of lights generated from said plurality of said light emitting units.

8. A photodetecting apparatus according to claim 4, wherein said light source means comprises a plurality of light emitting units, each generating light having a different wavelength, and a coupling unit for coupling a plurality of lights generated from said plurality of said light emitting units; and said photodetecting means comprises a light selecting unit for receiving light emerging from said scattering and absorption medium, selecting and emitting light having a predetermined wavelength, and a photodetecting unit for detecting light emitted from said light selecting unit.

9. A photodetecting apparatus according to claim 1, wherein said processing means comprises a reference signal generating unit for generating a reference signal having a reference frequency different from said predetermined frequency, a first signal converter for receiving said reference signal and said modulating signal, calculating a product of both signals, and thereafter generating a signal having a frequency difference between said reference frequency and said predetermined frequency and including phase information of said modulating signal against said reference signal, and a second signal converter for receiving said reference signal and said optically detected signal, calculating a product of both signals, and thereafter generating a signal having a frequency difference between said reference frequency and said predetermined frequency and including phase information of said modulating signal against said reference signal; and said processing means obtains one of the timing difference between said modulating signal and said optically detected signal, and the phase difference between said modulating signal and said optically detected signal, based on a waveform of the output signal of said first signal converter and a waveform of the output signal of said second signal converter.

10. A photodetecting apparatus comprising:

intensity tuneable light irradiating means for generating a first number of lights each having a different predetermined wavelength to irradiate a scattering and absorption medium, an intensity of each said light being modulated by a modulating signal having an ac component with a predetermined frequency, an amount of modulation of generating light or a quantity of generating light being adjustable in accordance with an external instruction;

light branching means for receiving optical signals each having said predetermined frequency component emerging from said scattering and absorption medium after said optical signals are generated from said intensity tuneable light irradiating means, irradiate said scattering and absorption medium and propagate in said scattering and absorption medium, and branching said optical signals into said first number of lights each having said predetermined wavelength;

photodetecting means comprising said first number of photodetecting units arranged for each said light having said predetermined wavelength, for detecting light emitted from said light branching means;

feedback means for receiving an optically detected signal for each said predetermined wavelength corresponding to the intensity of said optical signal for each said predetermined wavelength emitted from said photodetecting means, sending an instruction to said intensity tuneable light irradiating means to increase the quantity of generating light having the respective wavelength or to increase the amount of modulation of generating light having the respective wavelength when the intensity of an ac component of said optically detected signal detected by said photodetecting means is smaller than a predetermined value, and sending an instruction to said intensity tuneable light irradiating means to decrease the quantity of generating light having the respective wavelength or to decrease the amount of modulation of generating light having the respective wavelength when the intensity of the ac component of said optically detected signal detected by said photodetecting means is larger than the predetermined value; and processing means for receiving said modulating signal and said optically detected signals and obtaining one of a timing difference between said modulating signal and said optically detected signal, and a phase difference between said modulating signal and said optically detected signal, for each said predetermined wavelength.

11. A photodetecting apparatus according to claim 10, wherein said modulating signal is formed by superimposing one or more kinds of frequency components on a dc component.

12. An photodetecting apparatus according to claim 10, wherein light generated from said intensity tuneable light irradiating means is pulsed light.

13. An photodetecting apparatus according to claim 10, wherein said intensity tuneable light irradiating means comprises a modulating signal generating unit for generating said modulating signal on which said ac component with said predetermined frequency is superimposed;

said first number of light source means for receiving said modulating signal and generating lights, each having said different predetermined frequency, the intensity of each said light is modulated by said predetermined frequency; and said first number of light transmittivity varying units for varying light transmittivity for each said predetermined wavelength in accordance with a quantity-of-irradiation-light indicating signal sent from said feedback means for each said predetermined wavelength.

14. A photodetecting apparatus according to claim 10, wherein said intensity tuneable light irradiating means comprises said first number of modulating signal generating units for generating said modulating signal for each said predetermined wavelength, said ac component with said predetermined frequency being superimposed on said modulating signal, said modulating signal having an amplitude corresponding to a quantity-of-irradiation-light indicating signal sent from said feedback means for each said predetermined wavelength; and said first number of light source means for receiving said modulating signal and generating light having said predetermined wavelength, the intensity of said light being modulated by said predetermined frequency.

15. A photodetecting apparatus according to claim 13, wherein said light source means comprises a light emitting unit for generating light having a variable wavelength.

16. A photodetecting apparatus according to claim 13, wherein said light source means comprises a plurality of light emitting units, each generating light having a different wavelength; and a light selecting unit for selecting and taking out one of lights generated from said plurality of said light emitting units.

17. A photodetecting apparatus according to claim 13, wherein said light source means comprises a plurality of light emitting units, each generating light having a different wavelength, and a coupling unit for coupling a plurality of lights generated from said plurality of light emitting units; and said photodetecting means comprises a light selecting unit for receiving light emerging from said scattering and absorption medium, selecting and emitting light having a predetermined wavelength, and a photodetecting unit for detecting light emitted from said light selecting unit.

18. A photodetecting apparatus according to claim 10, wherein said processing means comprises a reference signal generating unit for generating a reference signal having a reference frequency different from said predetermined frequency, said first number of first signal converters for receiving said reference signal and said modulating signal for each said predetermined wavelength, calculating a product of said reference signal and said modulating signal for each said predetermined wavelength, and thereafter generating a signal having a frequency difference between said reference frequency and said predetermined frequency for each said predetermined wavelength, and a second signal converter for receiving said reference signal and said optically detected signal for each said predetermined wavelength, calculating a product of said reference signal and said modulating signal for each Said predetermined wavelength, and thereafter generating a signal having a frequency difference between said reference frequency and said predetermined frequency for each said predetermined wavelength; and said processing means obtains one of the timing difference between said modulating signal and said optically detected signal, and the phase difference between said modulating signal and said optically detected signal, for each said predetermined wavelength, based on a waveform of the output signal of said first signal converter and a waveform of the output signal of said second signal converter.

* * * * *